United States Patent [19]
Burgeson et al.

[11] Patent Number: 5,770,562
[45] Date of Patent: Jun. 23, 1998

[54] PRODUCTS AND METHODS FOR IMPROVING KERATINOCYTE ADHESION TO THE DERMIS

[75] Inventors: Robert E. Burgeson, Boston, Mass.; Gregory P. Lunstrum, Portland, Oreg.; Patricia Rousselle, Lyons, France; Douglas R. Keene, Portland; M. Peter Marinkovich, Beaverton, both of Oreg.

[73] Assignee: Oregon Health Sciences University, Portland, Oreg.

[21] Appl. No.: 469,500

[22] Filed: Jun. 6, 1995

Related U.S. Application Data

[63] Continuation of Ser. No. 319,064, Oct. 6, 1994, abandoned, which is a continuation of Ser. No. 966,974, Oct. 26, 1992, abandoned, which is a continuation-in-part of Ser. No. 936,850, Aug. 28, 1992, Pat. No. 5,352,668, which is a continuation-in-part of Ser. No. 675,563, Mar. 26, 1991, abandoned.

[51] Int. Cl.⁶ ............................. A61K 38/39; C07K 14/78
[52] U.S. Cl. ............................. 514/8; 435/402; 514/21; 530/395; 530/892
[58] Field of Search ............................. 530/395, 402, 530/408, 842, 850; 435/240.31, 435, 366, 371, 402; 514/8, 21

[56] References Cited

U.S. PATENT DOCUMENTS

| | | | |
|---|---|---|---|
| 4,829,000 | 5/1989 | Kleinman et al. | 435/240.23 |
| 4,870,160 | 9/1989 | Charonis et al. | 530/326 |
| 5,092,885 | 3/1992 | Yamada et al. | 623/11 |
| 5,120,828 | 6/1992 | Charonis | 530/326 |
| 5,352,668 | 10/1994 | Burgeson et al. | 514/21 |
| 5,444,158 | 8/1995 | Engrall et al. | 530/413 |

OTHER PUBLICATIONS

ATCC Catalogue of Cell Lines and Hybridomas, 6th ed., 1988, pp. 328, 381.
ATCC Catalogue of Cell Lines and Hybridomas, 7th ed., 1992, pp. 421, 506.
Stites et al, Basic and Clinical Immunology, 7th ed., published 1991 by Appleton & Lange (Norwalk), pp. 423–425.
Protein Purification Methods, Harris et al, published 1989 by IRL Press, pp. 9–10, 57–60, and 62.
Alstadt et al., "Effect of Basement Membrane Entactin on Epidermal Cell Attachment and Growth," J. Invest. Dermatol. 88:55–59 (Jan. 1987).

(List continued on next page.)

*Primary Examiner*—Jeffrey E. Russel
*Attorney, Agent, or Firm*—Klarquist Sparkman Campbell Leigh & Whinston, LLP

[57] ABSTRACT

The isolated proteins kalinin and k-laminin are disclosed to provide adhesion between epidermal keratinocytes and the underlying dermis. Purified kalinin localizes to the anchoring filaments of basement membranes of human subepithelial skin, trachea, esophagus, cornea and amnion when such areas are probed with BM165 monoclonal antibody after localization. The protein has a molecular weight of approximately 410–495 kDa and exists in a cell-associated form (about 495 kDa) and two medium-associated forms (about 460 and 410 kDa, respectively). The BM165 epitope is located on the 165-kDa and 200 kDa subunits. Kalinin has a rotary-shadow image revealing an asymmetric rod 107-nm long having two globules at a first end and a single globule at an opposing end. The k-laminin adhesion molecule is an isolated heterotrimeric laminin variant that has a molecular weight of about 650 kDa and separates on western blots into first and second fragments that are similar to the B1 and B2 fragments of laminin. K-laminin also includes a third fragment of 190 kDa that is not immunoreactive with monoclonal antibodies 1F5, 11D5 and 4C7, but is immunoreactive with a monoclonal antibody BM165. Kalinin and k-laminin are preferably covalently associated. A method is also disclosed for improving adhesion of transplanted keratinocytes to an underlying substrate, such as the human dermis, by optimizing production of kalinin from cultured keratinocytes, or by providing an exogenous source of kalinin between the keratinocytes and substrate.

3 Claims, 22 Drawing Sheets

OTHER PUBLICATIONS

Bächinger et al., "The Relationship of the Biophysical and Biochemical Characteristics of Type VII Collagen to the Function of Anchoring Fibrils," J. Biol. Chem. 265:10095–10101 (1990).

Boyce et al., "Cultivation, Frozen Storage, and Clonal Growth of Normal Human Epidermal Keratinocytes in Serum–Free Media," J. Tissue Culture Methods 9:83–93 (1985).

Carter et al., "Epiligrin, a New Cell Adhesion Ligand for Integrin α3β1 in Epithelial Basement Membranes," Cell 65:599–610 (May 17, 1991).

De Luca et al., "Polarized integrin mediates human keratinocyte adhesion to basal lamina," Proc. Natl. Acad. Sci. USA 6888–6892 (Sep. 1990).

Fine, "GB3 Antigen is an Accurate Marker of Only the Herlitz Subset of Junctional Epidermolysis Bullosa," Abstract, Clin. Res. 38(1) (1990).

Fine et al., "19–DEJ–1, A Hemidesmosome–Anchoring Filament Complex–Associated Monoclonal Antibody" Arch Dermatol 125:520–3 (1989).

Fisher, "Skin—The Ultimate Solution for the Burn Wound," New England J. of Medicine 311:466–467 (Aug. 16, 1984).

Gallico et al., "Permanent Coverage of Large Burn Wounds With Autologous Cultured Human Epithelium," The New England J. of Medicine 311:448–451 (Aug. 16, 1984).

Goldberg, "Is the lamina lucida of the basement membrane a fixation artefact?" European J. of Cell. Biol. 42:365–368 (1986).

Hancock, "Cultured keratinocytes and keratinocyte grafts," BMJ 299:1179–1180 (Nov. 11, 1989).

Heaphy et al., "The Human Cutaneous Basement Membrane–Anchoring Fibril Complex: Preparation and Ultrastructure," J. Invest. Dermatol. 68:177–186 (Apr. 1977).

Keene et al., "Kalinin: A Novel Basement Membrane Component Implicated in Keratinocyte Cell Adhesion," Abstract 2231, Basement Membrane Components (2218–2231) p. 401a (Not dated).

Konter et al., "Adhesion molecule mapping in normal human skin," Arch Dermatol Res 281:454–462 (1989).

Lunstrum et al., "Identification of a New Basement Membrane Antigen which Localizes to the Lamina Lucida and Displays a Novel Tissue Distribution," Abstract 61, Cell Attachment to Extracellular Matrix I (56–71) p. 15a (1989).

Lunstrum et al., "Large Complex Globular Domains of Type VII Procollagen Contribute to the Structure of Anchoring Fibrils," J. Biol. Chem. 261:9042–9048 (1986).

Morris et al., "The Tissue Form of Type VII Collagen Is an Antiparallel Dimer," J. Biol. Chem. 261:5638–5644 (1986).

Mortureux et al., "BM–600 Is Present in Normal Amniotic Fluid," Abstract, J. Invest. Dermatol. 95:481 (Oct. 1990).

O'Connor et al., "Grafting of Burns with Cultured Epithelium Prepared from Autologous Epidermal Cells," The Lancet, p. 75 (Jan. 10, 1981).

Phillips, "Cultured Skin Grafts—Past, Present, Future," Arch Dermatol 124:1035–1038 (Jul. 1988).

Rousselle et al., "Identification of a New Basement Membrane Antigen," Abstract in Western Connective Tissue Society Draft Program and Abstracts for Apr. 26–29, 1990, meeting, Santa Cruz, California.

Rousselle et al., "A Novel Basement Membrane Component Implicated in Keratinocyte Cell Adhesion," J. Cell Biol. 114:567–576 (1991).

Sakai et al., "Type VII Collagen Is a Major Structural Component of Anchoring Fibrils," J. Cell Biol. 103:1577–1586 (Oct. 1986).

Sakai et al., "Fibrillin, A New 35–kD Glycoprotein, Is a Component of Extracellular Microfibrils," J. Cell Biol. 103:2499–2509 (Dec. 1986).

Saksela et al., "Basal Lamina Components in Experimentally Induced Skin Blisters," J. Invest. Dermatol. 77:283–286 (1981).

Takashima et al., "Activation of Rabbit Keratinocyte Fibronectin Receptor Function In Vivo During Wound Healing," J. Invest. Dermatol. 86:585–590 (1986).

Thomas et al., "Cultured epithelia from junctional epidermolysis bullosa letalis keratinocytes express the main phenotypic characteristics of the disease," British J. Dermatol. 122:137–145 (1990).

Verrando et al., "The new basement membrane antigen recognized by the monoclonal antibody GB3 is a large size glycoprotein: modulation of its expression by retinoic acid," Biochemica et et Biophysica Acta 942:45–56 (1988).

Verrando et al., "Monoclonal Antibody GB3, a New Probe for the Study of Human Basement Membranes and Hemidesmosomes," Exp. Cell Res. 170:116–128 (1987).

Waikakul et al., "Application of Freeze–Dried Amniotic Membrane: A Control Trial at the Donor Site of Split–Thickness Skin Grafting," Bulletin of the Hospital for Joint Diseases Orthopaedic Institute 50:27–34 (1990).

Woodley et al., "Burn Wounds Resurfaced by Cultured Epidermal Autografts Show Abnormal Reconstitution of Anchoring Fibrils," JAMA 259:2566–2571 (May 6, 1988).

Alitalo et al., "Extracellular Matrix Components Synthesized by Human Amniotic Epithelial Cells in Culture," Cell 19:1053–1062 (Apr. 1980).

Aratani and Kitagawa, "Enhanced Synthesis and Secretion of Type IV Collagen and Entactin during Adipose Conversion of 3T3–L1 Cells and Production of Unorthodox Laminin Complex," J. of Biological Chem. 263:16163–16169 (Nov. 1988).

Davis et al., "Isolation and Characterization of Rat Schwannoma Neurite–promoting Factor: Evidence that the Factor Contains Laminin," The J. of Neuroscience 5:2662–2671 (Oct. 1985).

Donaldson and Mahan, "Epidermal cell migration on lamin-incoated substrates," Cell Tissue Res. 235:221–224 (1984).

Edgar et al., "Structural Requirements for the Stimulation of Neurite Outgrowth by Two Variants of Laminin and Their Inhibition by Antibodies," The J. of Cell Biology 106:1299–1306 (1988).

Ehrig et al., "Merosin, a tissue–specific basement membrane protein, is a laminin–like protein," Proc. Natl. Acad. Sci. USA 87:3264–3268 (May 1990).

Engel et al., "Shapes, Domain Organizations and Flexibility of Laminin and Fibronectin, Two Multifunctional Proteins of the Extracellular Matrix," J. Mol. Biol. 150:97–120 (1981).

Frenette et al., "Biosynthesis and Secretion of Laminin and Laminin–associated Glycoproteins by Nonmalignant and Malignant Human Keratinocytes: Comparison of Cell Lines from Primary and Secondary Tumors in the Same Patient," Cancer Research 48:5193–5202 (Sep. 1988).

Goodman et al., "Two Distinct Cell–binding Domains in Laminin Can Independently Promote Nonneuronal Cell Adhesion and Spreading," The J. of Cell Biology 105:589–598 (Jul. 1987).

Liesi and Risteli, "Glial Cells of Mammalian Brain Produce a Variant Form of Laminin," Experimental Neurology 105:86–92 (1989).

Marchisio et al., "Polarized Expression of Integrin Receptors ($\alpha_6\beta_4$ $\alpha_2\beta_1$,$\alpha_3\beta_1$, and $\alpha_v\beta_5$) and their Relationship with the Cytoskeleton and Basement Membrane Matrix in Cultured Human Keratinocytes," The J. of Cell Biology 112:761–773 (Feb. 1991).

Marinkovich et al., "Characterization of a Novel Laminin Isoform Produced by Human Keratinocytes In Vitro," J. Invest. Derm. 96:551 (Apr. 1991).

Olsen et al., "Human Laminin: Cloning and Sequence Analysis of cDNAs Encoding A, Bl and B2 Chains, and Expression of the Corresponding Genes in Human Skin and Cultured Cells," Laboratory Investigation 60:772–782 (1989).

Peters et al., "The Biosynthesis, Processing, and Secretion of Laminin by Human Choriocarcinoma Cells," The J. of Biological Chemistry 260:14732–14742 (1985).

Rousselle et al., "Kalinin: An Epithelium–Specific Basement Membrane Adhesion Molecule That Is a Component of Anchoring Filaments," The J. of Cell Biology 114:567–576 (Aug. 1991).

Terranova et al., "Role of Laminin in the Attachment of PAM 212 (Epithelial) Cells to Basement Membrane Collagen," Cell 22:719–726 (Dec. 1980).

Wilke and Skubitz, "Human Keratinocytes Adhere To Multiple Distinct Peptide Sequences of Laminin," J. Invest. Derm. 97:141–146 (Jul. 1991).

Woodley et al., Laminin Inhibits Human Keratinocyte Migration, J. of Cellular Physiology 136:140–146 (1988).

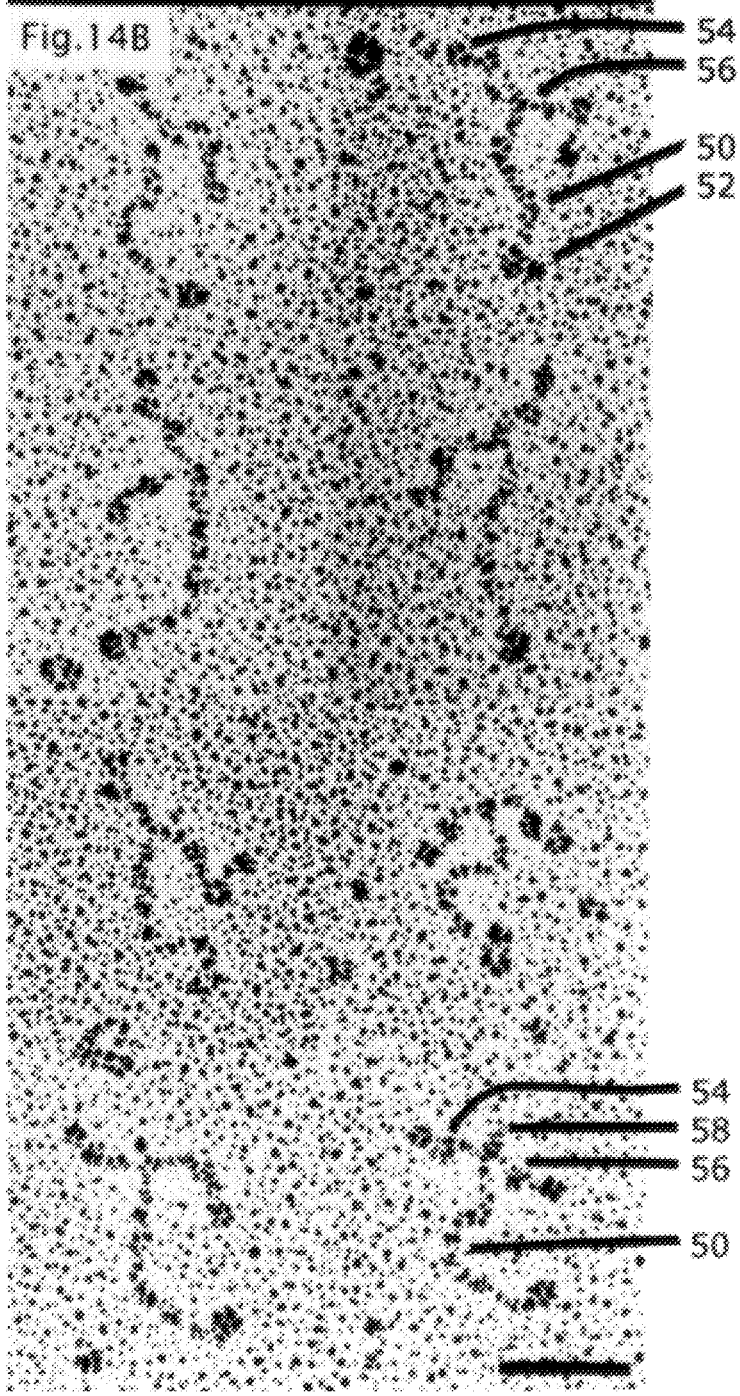

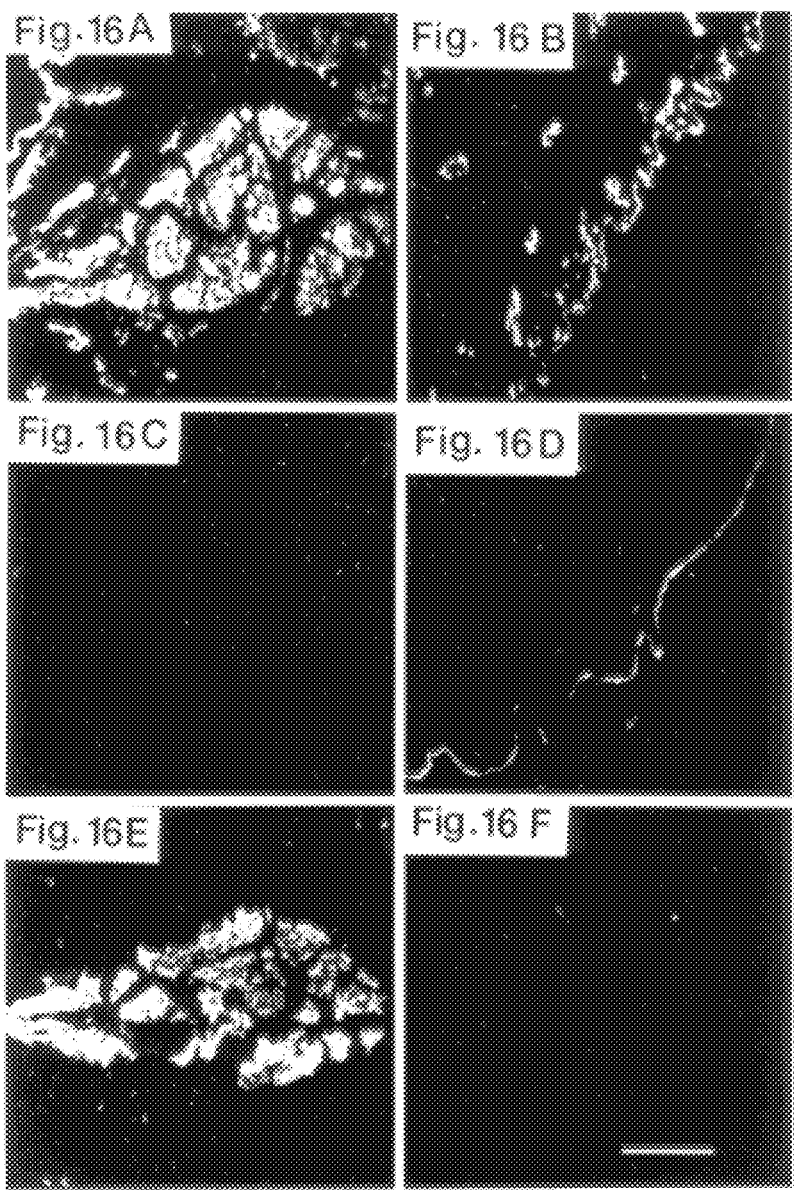

Fig. 19A  Fig. 19B Nonreduced

Fig. 19C  Fig. 19D Reduced

PRODUCTS AND METHODS FOR IMPROVING KERATINOCYTE ADHESION TO THE DERMIS

This application is a continuation of application Ser. No. 08/319,064, filed on Oct. 6, 1994, now abandoned, which was a continuation of application Ser. No. 07/966,974, filed on Oct. 26, 1992, now abandoned, which was a continuation-in-part of application Ser. No. 07/936,850, filed Aug. 28, 1992, now U.S. Pat. No. 5,352,668, which was a continuation-in-part of application Ser. No. 07/675,563, filed Mar. 26, 1991, now abandoned.

ACKNOWLEDGEMENT

This invention was made with Government support under grant number AR 35689 from the National Institutes of Health. The Government may have certain rights in this invention.

BACKGROUND OF THE INVENTION

1. Field of the Invention

This invention concerns basement-membrane proteins useful in adhering keratinocytes to the dermis. More specifically, this invention concerns a method of using these proteins to enhance the success of skin transplantation.

2. General Background of the Invention

The use of cultured epidermal grafts (keratinocyte grafts) to treat patients with life-threatening burns was first reported by O'Conner et al., *The Lancet* 1:75–78 (1981). Small skin biopsy specimens from burn patients were cultured in vitro, and the cultured autografts were placed on full thickness wounds on the arms of burn patients. The cultured keratinocytes successfully grew to cover the wounds in six weeks. Subsequent attempts have been made to improve this method by modifying it to grow keratinocytes in serum-free medium. Others have suggested using composite cadaver skin allografts resurfaced with autologous cultured keratinocytes. Attempts have also been made to use different backing materials for the cultured cells or to vary the keratinocyte culture methodology. The results of cultured keratinocyte transplants, however, have often been disappointing.

One of the most useful applications for keratinocyte grafts has been in patients with burns damaging more than half of the body surface. Such patients have insufficient donor sites to provide enough split skin thickness grafts to resurface the area of the burn after surgical excision. Unfortunately, the results of keratinocyte autografting in these circumstances have been variable and disappointing. Cultured epidermal grafts have been found to be significantly more fragile than normal skin and more prone to blistering. Woodley et al., JAMA 259:2566–2571 (1988). Some researchers have suggested that an abnormality in one or more connective tissue components within the autografts might explain the altered epidermal-dermal adherence observed clinically. The identity of that component, however, has remained obscure.

Laminin is a previously described noncollagenous glycoprotein. This molecule is a high molecular weight (850 kDa) extracellular matrix glycoprotein found almost exclusively in basement membranes. The basement membrane is a ubiquitous, specialized type of extracellular matrix that separates organ parenchymal cells from interstitial collagenous stroma. Interaction of cells with this matrix is an important aspect of both normal and neoplastic cellular processes.

Laminin purified from the murine Engelbreth-Holm-Swarm (EHS) tumor, is a disulfide bonded trimer consisting of a 400 kDa A chain, a 220 kDa B1 chain and a 210 kDa B2 chain (Cooper et al., *Eur. J. Biochem.* 119:189–197 (1981)). By rotary shadowing electron microscopy, EHS laminin has the image of an asymmetric cross with one long arm and three short arms (Engel et. al., *J. Mol. Biol.* 150:97–120 (1981)). Fragmentation studies of the large EHS laminin molecule have facilitated the localization of several of its properties to individual molecular domains. The large size and multidomain structure of this molecule give it the potential to span the basement membrane, mediate the interactions of multiple basement membrane components, and interact with receptors at basal cell surfaces adjacent to basement membrane. Several extracellular matrix proteins are capable of interacting with EHS laminin, including type IV collagen, nidogen, and heparin sulfate proteoglycan.

Many types of cells including keratinocytes (Stanley et al., *J. Invest. Dermatol.* 82:456–459 (1982)) and dermal fibroblasts (Woodley et al., *J. Cell. Physiol.* 136:140–146 (1988)) have been shown to synthesize laminin in culture. Some cell lines, including choriocarcinoma cells (Peters et al., *J. Biol. Chem.* 260:14732–14742 (1985)) and HT 1080 fibrosarcoma cells (Alitalo et al., *Cell* 19:1053–1062 (1980)) synthesize an excess of B chains relative to A chain. Pertinent to these observations, recent in situ hybridization experiments of human skin samples have revealed abundant expression of B1 and B2 chain genes, but undetectable expression of A chain gene (Olsen et al., *Lab Invest.* 60:772–782 (1989)). It is possible that in both skin and cultured cells, B1 and B2 chains are synthesized in relative excess and that synthesis of A chains serves as the rate limiting step for laminin assembly.

Additionally, laminin chains are apparently assembled into a variety of structures. Merosin is a laminin variant which contains a B1 chain, a B2 chain, and a third chain distinct from the A chain, although it shares 40% homology by sequence analysis (Ehrig et al., *Proc. Natl. Acad. Sci.* 87:3264–3268 (1990)). Mouse heart laminin is a laminin variant with a substituted A chain of a size similar to the one in merosin (Paulsson and Saladin, *J. Biol. Chem.* 264:18726–18732 (1989)). S-laminin, another laminin variant, contains a normal A chain, B2 chain, and a variant chain that shows some sequence homology to the B1 chain (Hunter et al., *J. Cell Biol.* 113:971–978 (1989)). Recently, the merosin variant chain and the S-laminin variant chain have been found complexed together with B2 in certain tissues, including the myotendonous junction (Engvall et al., *J. Cell Biol.* 1:731–740 (1990)). Two other laminin variants which apparently lack an A chain have been reported, but unlike merosin and S-laminin, it is not known whether they are present in tissue. These include rat RN22 schwannoma laminin (Davis et al., *J. Neurosci.* 5:2662–2671 (1985); Edgar et al., *J. Cell Biol.* 106:1299–1306 (1988); and 3T3 adipocyte laminin, Aratani and Kitigawa, *J. Biol. Chem.* 263:16163–16169 (1988)). These forms contain B1 and B2 subunits, but lack electrophoretically normal A subunits. Thus laminin exists as a family of proteins. Its individual members have restricted tissue distributions, for example merosin and S-laminin localize to muscular and neural basement membranes respectively, but not to epithelial basement membranes.

Laminin influences the growth and differentiation of many types of cells, and is present at the earliest stages of human development. Laminin is also a component of the extracellular matrix deposited by keratinocytes onto culture substratum (Carter et al., *J. Cell Biol.* 111:3141–3154

(1990); Marchisio et al., *J. Cell Biol.* 112:761–773 (1991)). Exogenously supplied EHS laminin facilitates the attachment of a variety of epithelial cell types (Terranova et al., *Cell* 22:719–726 (1980); Goodman et al., *J. Cell Biol.* 105:595–610 (1987)), including human keratinocytes (Wilke and Skubitz, *J. Invest. Dermatol.* 97:141–146 (1991)) but markedly decreases motility of cultured keratinocytes (Woodley et al., *J. Cell. Physiol.* 136:140–146 (1988)). This marked reduction in the motility of cultured keratinocytes is an impediment to the use of EHS laminin as an adhesion protein for transplanted keratinocytes. Inhibition of keratinocyte migration would diminish the ability of a cultured sheet of keratinocytes to spread out over a wound surface and completely cover an epidermal defect. Hence EHS laminin is not believed to be suitable for use in keratinocyte transplantation.

It is an object of this invention to identify and provide a therapeutically useful form of a newly isolated connective tissue component that provides epidermal-dermal adherence.

It is another object of this invention to use such a therapeutically useful substance to enhance the adhesion of transplanted cultured keratinocytes to an underlying substrate, such as a mammalian or human dermis.

Yet another object is to provide such a therapeutic substance that has minimal inhibition of keratinocyte migration.

These and other objects of the invention will be understood more clearly by reference to the followings detailed description.

SUMMARY OF THE INVENTION

The foregoing objects have been achieved by identification and production of several isolated and purified novel proteins that are present in the anchoring filaments of the basement membranes of human subepithelial skin, trachea, esophagus, cornea and amnion. One of these novel proteins, which has been named kalinin by its discoverers, has been found to provide adhesion between the human dermis and epidermis. This protein is also involved in the attachment of keratinocytes to solid substrates in vitro and to the basement membrane in vivo.

Kalinin exists in several forms having molecular weights in the range of about 410 to about 495 kDa. Kalinin separates on western blots into distinct subunits after disruption of disulfide bonds in the intact molecule. One form of kalinin is termed the "KC" form and is present in a "cell" fraction (associated with cells such as within cells or associated with a cell layer in cultures). The KC form has a molecular weight of about 495 kDa. When its disulfide bonds are disrupted, the KC form is separable into a 200-kDa subunit, a 155-kDa subunit, and a 140-kDa subunit.

Two other types of kalinin are termed the "KM1" and "KM2" forms which tend to accumulate in cell-culture medium bathing kalinin-producing cells under particular calcium concentrations. The KM1 form has a molecular weight of about 460 kDa and accumulates in media under low (0.035 mM) calcium concentrations. When its disulfide bonds are disrupted, KM1 is separable into a 165-kDa subunit, a 155-kDa subunit, and a 140-kDa subunit. The KM2 form has a molecular weight of about 410 kDa and accumulates in medium under a high (1.0 mM) calcium concentration. When its disulfide bonds are disrupted, KM2 is separable into a 165-kDa subunit, a 140-kDa subunit, and a 105-kDa subunit. The 140-kDa subunits of KC, KM1, and KM2 appear to be identical. The 165-kDa subunit of KM1 and KM2 appear to be derived from extracellular processing of the 200-kDa subunit of KC. The 155-kDa subunit of KC appears to be identical to the 155-kDa subunit of KM1. Thus, during conversion of KC to KM1, the 200-kDa subunit is processed to 165 kDa and, during conversion of KM1 to KM2, the 155-kDa subunit is processed to 105 kDa. An epitope of the 165-kDa subunit is recognized by monoclonal antibody BM165.

Rotary shadow imaging of the 460-kDa form of kalinin reveals an asymmetric 107-nm long rod having two small globules at a first end and a single large globule at the opposite end. The 410-kDa form appears to lack the second small globule at the first end. Kalinin has been found to be absent in the dermal-epidermal junction of humans with diseases such as junctional epidermolysis bullosa (Herlitz's variety), in which the epidermis separates from the underlying dermis.

Immunolocalization of kalinin to human skin demonstrates that this antigen is the ultrastructural element known as the anchoring filament. The rod-like shape and the length demonstrated by rotary shadowing of kalinin is also consistent with this role. The finding that most kalinin localizes to the lamina densa following antibody-induced rupture of the dermal-epidermal junction suggests that the BM165 antibody epitope lies near the region of the kalinin molecule responsible for binding to the hemidesmosome. The opposite end of the antigen appears to be buried in the lamina densa.

Yet another adhesion protein of the present invention is a laminin variant produced by keratinocytes and which the present inventors have named k-laminin. This isolated variant has a molecular weight of about 650 kDa and separates on western blots into three fragments. The first and second fragments are substantially identical to the B1 and B2 fragments of EHS laminin, and have molecular weights of 220 kDa and 210 kDa respectively. The third fragment has a molecular weight of about 190 kDa, and is not immunoreactive with laminin anti-A chain monoclonal antibodies 1F5, 11D5 and 4C7, but is immunoreactive with monoclonal antibody BM 165 against the 165K and 200K chains of kalinin. Hence the 620 kDa protein is a novel variant of laminin possessing a 190 kDa subunit that includes a BM165 epitope.

In the isolated k-laminin molecule, the B1, B2 and third chains are present in a ratio of about one chain of B1 to one chain of B2 to one chain of the 190 kDa fragment. This ratio is consistent with a heterotrimeric molecule that in isolation contains a single 220 kDa B1 chain, a single 210 kDa B2 chain, and a single 190 kDa chain. The 190 kDa chain is shorter than the EHS laminin A chain by about 240 kDa, and is immunologically unrelated to the laminin A chain, as evidenced by the absence of an antigen-antibody reaction between the 190 kDa chain and mAbs 1F5, 11D5 and 4C7. Instead, the variant 190 kDa chain shows structural and immunological similarity to the 200 kDa chain of kalinin that is processed to a 165 kDa chain.

The k-laminin molecule has a Y-shaped and not a cross-shaped rotary shadow image, with a long arm and two short arms. Globular domains are present at the distal end of each of the short arms and at the distal end oil the long arm. This rotary shadowed image shows that the short arm normally contributed by the laminin A chain is missing. The substituted 190 kDa chain contributes instead the large globule at the end of the long arm. A small globular domain is also present in some images at the intersection of the first and second short arms.

The k-laminin is immunoreactive with monoclonal antibody BM 165 (which crossreacts with both kalinin and k-laminin) but not monoclonal antibody K140 (which recognizes the 140 kDa fragment of kalinin but does not react with k-laminin). K-laminin does not naturally occur in the basement membrane of human skeletal muscle, blood vessel endothelium and peripheral nerve where other laminin variants are found. K-laminin is found, however, in amniotic fluid and the basement membrane zone of the dermal-epidermal junction in human skin, and is produced by squamous cell carcinoma line SCC-25.

Yet another novel protein of this invention is a covalent adduct between k-laminin and kalinin. The isolated adduct includes a molecule of k-laminin that includes first and second electrophoretic fragments substantially electrophoretically identical to a B1 and a B2 fragment of EHS laminin, and a third fragment of 190 kDa that is not immunoreactive with monoclonal antibodies 1F5, 11D5 and 4C7 but is immunoreactive with monoclonal antibody BM 165. A kalinin molecule is covalently attached to the k-laminin, and has the properties described above for kalinin. The adduct is immunoreactive with both polyclonal anti-kalinin and polyclonal anti-laminin, and reduction of the adduct yields a pattern of seven electrophoretic bands on a western blot that correspond to fragments of 105, 140, 145, 165, and 190 kDa, and B1 and B2 chains of laminin. The 145 kDa band is a proteolytic product of that 165 kDa chain.

Rotary shadow image analysis of the k-laminin/kalinin complex reveals an isolated molecule that has two short arms and two long arms. The length distribution of the long arms is bimodal with the first long arm having a length of about 81 nm and the second long arm having a length of about 103 nm. The 81 nm arm is consistent with the length of the long arm of k-laminin, and the 103 nm length is consistent with the total length of a kalinin molecule. The shadow image of this k-laminin/kalinin adduct differs substantially from the shadow image of laminin, which is an asymmetric cross with three short arms 37 nm long and one long arm 77 nm long. The three short arms in laminin each have two globular domains, and the long arm exhibits a single large terminal globular domain.

The invention also encompasses a method of improving adhesion of transplanted keratinocytes to an underlying substrate by providing an amount of the protein or proteins of the present invention between the keratinocytes and substrate. The amount of the protein is greater than the amount produced naturally by keratinocytes. This increased amount of kalinin, k-laminin or k-laminin/kalinin adduct, can be supplied by applying an exogenous supply of one or more of these proteins to the substrate, such as a wound surface or to the basal surface of a confluent layer of cultured keratinocytes prior to placing the layer on a graft site. The protein or proteins may be supplied in a pharmaceutically acceptable carrier, preferably in amounts of 1–10 µg/ml, or even in greater amounts such as greater than 40 µg/ml.

According to another aspect of the present invention, as an alternative to applying the protein or proteins to cultured keratinocyte cells prior to transplantation, the cultured keratinocytes can be induced to increase their basal levels of production of these substances to supra-physiologic levels by exposing the cells to growth promoters such as cytokines. Alternatively according to yet another aspect of the present invention, keratinocytes are monitored during culturing to determine the time when they are actively producing kalinin, k-laminin, or adducts thereof; the keratinocytes are transplanted to a substrate before active production by the cells of one or more of these substances declines significantly.

BRIEF DESCRIPTION OF THE DRAWINGS

FIG. 1A is a photomicrograph showing the indirect immunofluorescent localization of the BM165 antigen in human foreskin, while

FIG. 4C is a scanning electron micrograph of cells prepared as in FIG. 4A, while

FIGS. 8A–8E are photographs at varying magnifications showing rotary shadow analysis of the BM165 antigen following affinity purification, the bar representing a length of 100 nm.

FIGS. 14A and 14B show rotary shadow imaging analysis of k-laminin and laminin from affinity purified squamous cell carcinoma medium.

FIG. 16A, FIG. 16B, FIG. 16C, FIG. 16D, FIG. 16E and FIG. 16F are a series of photomicrographs comparing laminin distribution in peripheral nerve (FIG. 16A, FIG. 16C and FIG. 16E) and neonatal human foreskin (FIG. 16B, FIG. 16D and FIG. 16F) analyzed by indirect immunofluorescent microscopy with polyclonal anti-laminin (FIG. 16A and FIG. 16B); poly-clonal anti-kalinin FIG. 16C and FIG. 16D; Mab 5H2 anti-merosin (FIG. 16E), and polyclonal anti-kalinin, preimmune serum (FIG. 16F).

DESCRIPTION OF PREFERRED EMBODIMENTS

Figure 9:
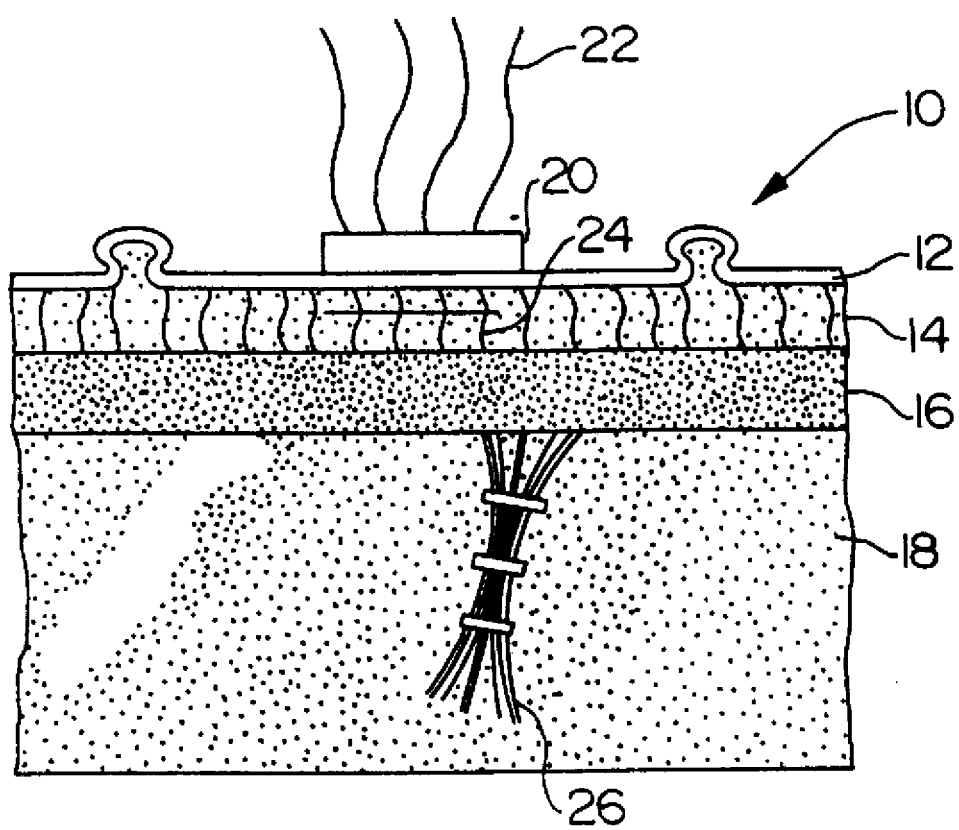
FIG. 9 is a schematic diagram of the ultrastructure of the basement membrane region at the dermal-epidermal junction of human skin.

The ultrastructure of the basement membrane at the epidermal-dermal junction is shown schematically in FIG. 9, which depicts the lower part of a basal keratinocyte 10 having a plasma membrane 12 that seats on a lamina lucida 14, subadjacent lamina densa 16, and dermis 18. A hemidesmosome 20 is depicted at the basal portion of keratinocyte 10 on plasma membrane 12. Tonofilaments 22 insert into the hemidesmosome 20 and extend into the cytoplasm. Anchoring filaments 24 arise from the plasma membrane beneath the attachment plaque of hemidesmosome 20. The filaments traverse the lamina lucida 14 and connect the basal plasma membrane 12 with the lamina densa 16, and are most numerous in the region of the hemidesmosome. Anchoring fibrils 26, in contrast, are short curved structures, with an irregularly spaced cross banding of their central portions, which fan out at either end. The distal part of fibrils 26 inserts into the lamina densa while the proximal part terminates in the papillary dermis or loops around to merge into the lamina densa. One aspect of the present invention concerns a protein associated with the anchoring filaments 24, which performs an important function in adhering the dermis to the epidermis.

The ultrastructure of the anchoring fibril network suggests that it secures the basement membrane to the underlying dermis. Susi et al., *J. Cell Biol.* 34:686–690 (1967); Kawanami et al., *Am. J. Pathol.* 92:389–410 (1978). This hypothesis is supported by observations that individuals with recessive dystrophic epidermolysis bullosa lack anchoring fibrils (Briggaman et al., *J. Invest. Dermatol.* 65:203–211 (1975); Leigh et al., *J. Invest. Dermatol.* 90:612–639 (1988); Bruckner-Tuderman et al., *J. Invest. Dermatol.* 93:3–9 (1989)) and suffer from spontaneous separation of the epidermal basement membranes from the subadjacent stroma.

The present inventors describe herein several proteins according to the present invention that are associated with anchoring filaments. These proteins are further characterized by ultrastructural location and tissue distribution. The proteins have been purified and their filamentous conformations determined by shadow imaging. Finally, kalinin is shown to be necessary for the in vitro attachment of keratinocytes to plastic or glass substrates and to the basement membrane in vivo.

Source of Kalinin Immunogen

Kalinin is localized using the monoclonal antibody BM165, which was prepared using a "BM165 immunogen."

The BM165 immunogen was derived from an extract of human amnion, prepared as follows. Collagenase extraction and purification of the NC-1 globular domain of type VII collagen from human amnion has been described previously. Bächinger et al., *J. Biol. Chem.* 265:10195–10101 (1990), which is incorporated herein by reference. During one step of this purification, the extract is incubated with DEAE-cellulose (DE52, Whatman) in a low salt buffer (2M urea, 25 mM NaCl, 5 mM EDTA and 50 mM Tris-HCl, pH 7.8). The unbound fraction was used in the further purification of the NC-1 domain. The DEAE-cellulose was washed with an equal volume of buffer containing 0.2M NaCl and the eluted material was isolated after centrifugation at 17,000×g for 60 min. The sample was concentrated 10-fold by ammonium sulfate precipitation (50% saturation) and equilibrated in PBS (phosphate-buffered saline) by dialysis. The resulting complex mixture of proteins served as an immunogen in the preparation of hybridomas against kalinin.

Keratinocyte Cell Culture

Human foreskin keratinocytes were prepared according to the published procedures of Boyce et al., *J. Tris. Cult. Meth.* 9:83–93 (1985), which are incorporated herein by reference. Cells were grown in Keratinocyte Growth Medium (KGM) containing 0.15 mM $CaCl_2$ and subcultured according to the manufacturer's instructions (Clonetics). For most immunocytochemical experiments, first- or second-passage cells were grown in glass or plastic chamber slides (Lab-Tek) or on glass cover slips to approximately 80 percent confluency. For large-scale collection, spent-media cells were grown in 150-$cm^2$ tissue culture dishes and fed three times per week with 15 mL fresh media.

Affinity Purification of the BM165 Antigen

Media collected from growing keratinocytes was clarified by centrifugation at 2,000×g for 10 min. Endogenous protease activity was minimized by the addition of EDTA, PMSF (phenylmethylsulfonyl fluoride) and N-ethylmaleimide to final concentrations of 5 mM, 50 μM, and 50 μM, respectively. The media was sterilized by filtration and either processed immediately or stored frozen at −20° C. until use.

BM165 monoclonal antibodies (mAbs) were conjugated to CNBr-activated Sepharose 4B (Pharmacia LKB, Inc.), at 1 mg of antibody per mL of resin, as described by the manufacturer. Keratinocyte medium (1–2 liters) was passed through a 15-mL column of the conjugated antibodies and the column was washed with PBS. The BM165 antigen was eluted with 1M acetic acid and fractions were monitored for absorbance at 280 nm. Pooled fractions were treated with diisopropylfluorophosphate (5 μg/mL) and dialyzed against appropriate buffers for further analysis.

To perform SDS-PAGE (sodium dodecyl sulfate-polyacrylamide gel electrophoresis) of the eluted fractions, samples of the fractions were separated on 3–5% gradient gels before reduction and on 5% gels after reduction with β-mercaptoethanol. In addition to high molecular weight pre-stained standards (Biorad), the NC-1 domain of disulfide-bonded type VII collagen ($M_r$=450,000 daltons), reduced NC-1 domains ($M_r$=150,000 daltons) and reduced fibrillin ($M_r$=350,000 daltons) (Sakai et al., *J. Cell Biol.* 103:1577–1586 (1986)) were used in determining $M_r$ scales.

Tissue Preparation

Enbloc immunolocalization of antigens was performed as previously described by Keene et al., *J. Cell Biol.* 104:611–621 (1987), with some modifications as follows:

Human neonate foreskins collected shortly after circumcision were cut into 0.5 mm×1 mm blocks, all including epithelium, and washed for two hours in phosphate buffered saline (PBS), pH 7.4 at 4° C., rinsed in several changes of PBS over 6 hours, then incubated overnight at 4° C. in 1-nm gold-conjugated secondary antibody (Janssen Life Sciences Products, Piscataway, N.J.) diluted 1:3 in PBS containing 1.0% BSA (bovine serum albumin). Following washing, the foreskin tissues were submersed in ice-cold silver intensification solution (Janssen Life Sciences Products, Piscataway, N.J.) for 15 minutes, then rapidly warmed to room temperature. After allowing silver to precipitate upon the 1-nm gold particles for seven minutes at room temperature, the tissues were rinsed several times over a 15-minute period with water, then rinsed with 0.1M cacodylate buffer at pH 7.4. The tissues were finally fixed in 0.1-M cacodylate-buffered 1.5%/1.5% glutaraldehyde/paraformaldehyde, pH 7.4, dehydrated in a graded series of ethanol dilutions, exposed to propylene oxide, and embedded in Spurrs epoxy.

Figures 2A, 2B:
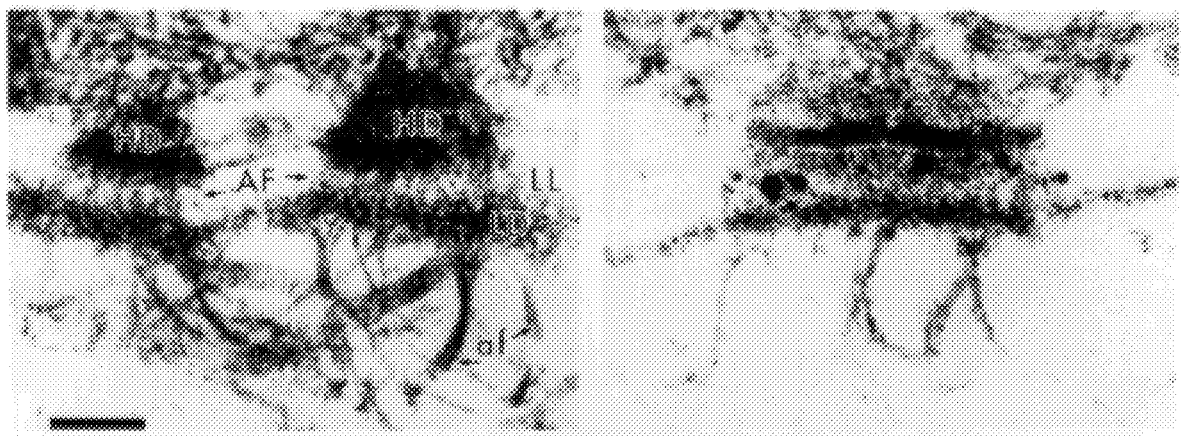
FIG. 2A is a photomicrograph of the dermal-epidermal junction in human skin showing the ultrastructural features of this region, the bar representing a length of 100 nm.
FIG. 2B is a photomicrograph similar to FIG. 2A showing localization of BM165 monoclonal antibody to the anchoring filaments of the dermal-epidermal basement membrane.

Control antibodies used included those recognizing elastin (produced and provided by Dr. Lynn Sakai), collagen type IV (Sakai et al.,*Am. J. Pathology* 108:310–318 (1982)), and collagen type VI (Keene et al, *J. Cell. Biol.* 107:1995–2006 (1988)). One sample of skin was fixed for 30 minutes in ice-cold acetone, rinsed in buffer, further fixed in 3%/3% aldehydes and 1% $OsO_4$, then dehydrated in acetone prior to embedding in Spurrs epoxy in order to demonstrate the presence of anchoring filaments (FIG. 2A).

Electron Microscopic Examination

For examination of normal cell ultrastructure prior to antibody treatment, human keratinocyte cultures were grown on glass coverslips and fixed in 0.1-M cacodylate-buffered 1.5%/1.5% glutaraldehyde/paraformaldehyde, 1.0% $OsO_4$. The cultures were dehydrated in a graded ethanol series, then either embedded directly in Spurrs epoxy for transmission electron microscopy (TEM), or critical-point dried and sputter-coated for scanning electron microscopy (SEM) as previously described (Keene et al.,*J. Cell. Biol.* 107:1995–2006 (1988)).

TEM immunoelectron microscopy was performed on keratinocytes grown on 8-well permanox culture flasks using an identical protocol as that described above for tissues, except that (a) the incubation time in primary antibody was four hours at room temperature; (b) the secondary antibody was conjugated to 5-nm gold and diluted 1:3 in BSA buffer (20 mM Tris-HCl, 0.9% NaCl, 1 mg/mL BSA, 20 mM $NaN_3$); and (c) the silver-intensification procedure was omitted.

Keratinocytes grown on glass coverslips and observed by SEM following exposure to antibody were treated identically, except they were critical-point dried from liquid $CO_2$ following dehydration in ethanol.

For routine TEM examination, 60- to 90-nm thick sections were cut on a Reichert ultramicrotome using diamond knives. The sections were contrasted in uranyl acetate and Reynolds lead citrate (Reynolds, *J. Cell Biol.* 17:208–215 (1963)) and examined using a Philips 410 LS TEM instrument operated at 60 kV. For routine SEM examination, samples were sputter-coated with a minimum amount of gold-palladium and observed in the upper stage of a scanning electron microscope (Model DS130; International Scientific Instruments, Inc., Milpitas, Calif.) operated at 10 kV, using a spot size of 3–10 nm.

Other Techniques

Methods including western blotting, rotary-shadow analysis and length measurements have been detailed elsewhere (Morris et al.,*J. Biol. Chem.* 261:5638–5644 (1986); Lunstrum et al., *J. Biol. Chem.* 261:9042–9048 (1986); and Bächinger et al.,*J. Biol. Chem.* 265:10095–10101 (1990)).

Rotary shadowing of molecules was accomplished using a modification of standard techniques described by Shotton et al., *J. Mol. Biol.* 131:303–329 (1979) and Tyler et al., *J. Ultrastruct. Res.* 71:95–102 (1980). Samples in 0.15-M carbonate buffer, pH 7.4, were diluted with glycerol to a final concentration of 70%. Then, 100 μL of solution were sprayed through an airbrush at an acute angle onto freshly cleaved 6-mm diameter mica discs. Droplet diameters were 50–200 μm. Samples were dried in an evaporator at $10^{-6}$ Torr. Platinum wire was wrapped around the carbon electrodes and the sample was placed on the stage and rotated at 100 rpm. At high voltage, the platinum was evaporated to completion at a 6-degree angle from the mica surface. The stage was then tilted 90 degrees relative to a carbon source and the chamber was evacuated. A 50-Å layer of carbon was evaporatively deposited onto the surface of the mica to form a "carbon replica." The carbon replica was immediately floated off the mica by carefully immersing the carbon-coated mica in double-distilled water. The carbon replicas were mounted onto 400-mesh grids. The replicas were examined using a transmission electron microscope at 80 kV with a 30 μm objective aperture.

BM165 Hybridoma and Monoclonal Antibody Preparation

Hybridomas were prepared and screened by indirect immunofluorescence as previously described. Sakai et al. *J. Cell Biol.* 103:1577–1586 (1986). The BM165 mAb, an $IgG_1$, was purified from cell culture supernatants as described elsewhere (Keene et al.,*J. Cell Biol.* 113:971–978 (1991)). Several monoclonal antibodies were provided by Dr. Eva Engvall of the La Jolla Cancer Research Foundation, which included the following: 11D5 mAb (Engvall et al., *Cell Regulation* 1:731–740 (1990)), 4C7 mAb specific for the laminin A chain (Engvall et al., *J. Cell Biol.* 103:2457–2465 (1986)), and 4E10 mAb specific for the laminin B chain (Wewer et al., *J. Biol. Chem.* 258:12654–12660 (1983)). Rabbit polyclonal antiserum against mouse laminin was obtained from Sigma Chemical Company of St. Louis, Mo.

Monoclonal antibodies were raised to a mixture of partially purified proteins originally extracted from human amnion by collagenase digestion as described for the isolation of the type VII collagen NC-1 domain. Bächinger et al., J. Biol. Chem. 265:10095–10101 (199). The resulting hybridomas were screened by indirect immunofluorescence for localization to the dermal-epidermal zone, but not to the vascular basement membrane zone, of human fetal foreskin. Selected hybridomas were rescreened by western blotting of the immunogen and protein extracts containing known basement membrane components. Hybridomas that did not recognize known basement membrane components were retained for further study.

Figure 1A:
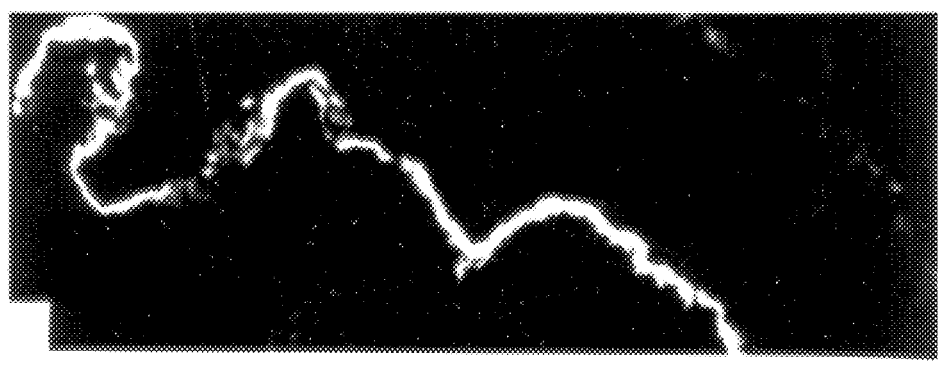

One of the aforesaid screenings produced two hybridomas that appeared to recognize the same unique protein. One of these, termed BM165, was used for the studies reported here. The monoclonal antibody produced by the BM165 hybridoma, also termed BM165, specifically identifies the dermal-epidermal junction basement membrane zone of skin, but shows no reactivity to the basement membranes of the vasculature or surrounding nerves (FIG. 1A and FIG. 1B.

Tissue Distribution of BM165 Mab immunoreactivity

The tissue distribution of BM165 mAb reactivity is shown in Table I. All of the subepithelial regions of skin, trachea, esophagus, cornea and amnion exhibited crisp, brilliant, continuously linear fluorescence. The tissue distribution of fluorescence directly paralleled the occurrence of hemidesmosomes and anchoring fibrils, with the exception of occasional and weak staining of the intestinal smooth muscles. No BM165 mAb reactivity was observed in tissue from human kidney, blood vessels, nerve, and cartilage.

TABLE I

Tissue Distribution of Antigen Recognized by BM165 mAbs As Determined by Indirect Immunofluorescence

| Tissue | Result |
|---|---|
| Skin, subepithelial | + |
| Trachea, subepithelial | + |
| Esophagus, subepithelial | + |
| Cornea, subepithelial | + |
| Amnion, subepithelial | + |
| Intestinal smooth muscle | +/− |
| Kidney | − |
| Blood vessels | − |
| Nerve | − |
| Cartilage | − |

The BM165 mAb was then used to localize the corresponding antigen within the dermal-epidermal basement membrane of human foreskin. Primary antibody was localized using secondary antibody conjugated to 1 nm gold, which was visualized by silver enhancement. The use of 1-nm gold was necessary due to the limited penetration of the basement membrane by a 5-nm gold-conjugated secondary antibody.

Figure 2C:
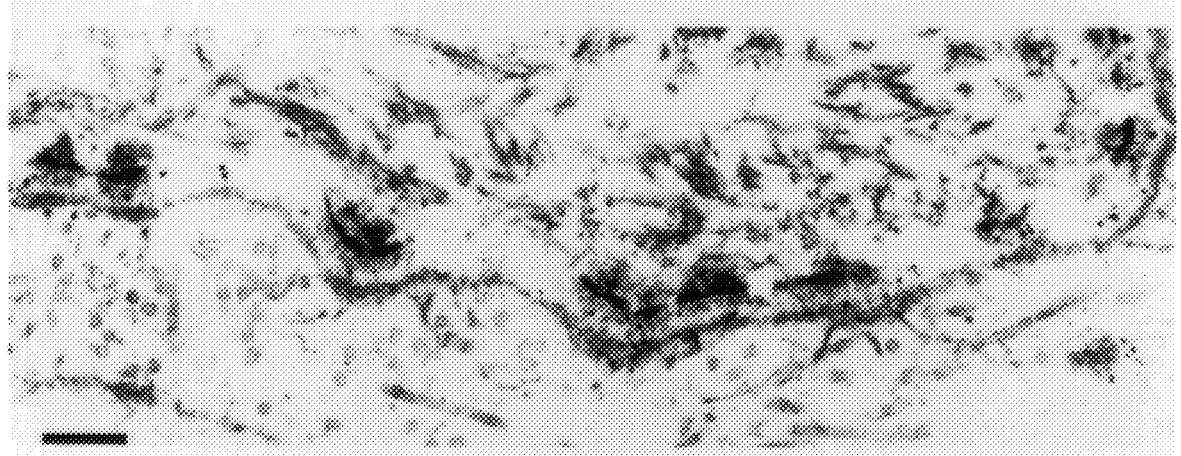
FIG. 2C shows labeling with monoclonal antibody BM165 along a continuous stretch of intact, skin, the bar representing a length of 200 nm.

This procedure localized the BM165 antigen to the anchoring filaments, just below the basal dense plate of hemidesmosomes (FIG. 2B and 2C). No labeling of the anchoring filaments was seen when an antibody of irrelevant specificity was employed as the primary antibody (data not shown). Some additional label was observed along the lamina densa (FIG. 2C), but the majority of the label appeared beneath the hemidesmosomes. Small amounts of gold deposits were also seen beneath the dermal side of the lamina densa.

Figure 2D:
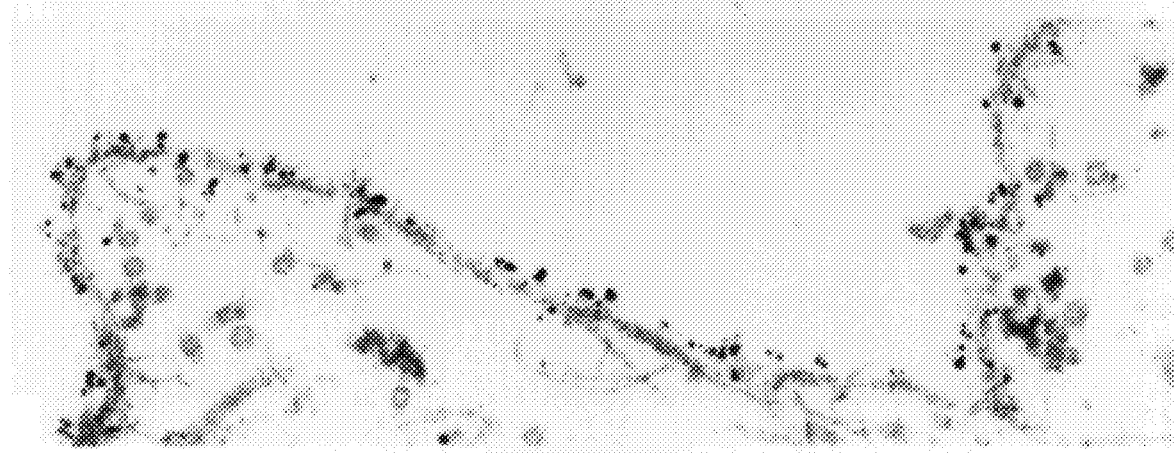
FIG. 2D shows labeling with monoclonal antibody BM165 along the basement membrane in a region where the antibody has induced epidermal detachment.

Throughout these experiments, extensive, often complete de-epithelization of skin samples during incubation with the primary antibody was commonly observed. This was entirely outside the inventors' considerable experience with use of antibodies to type-IV and type-VII collagens. The regions of unsplit basement membrane shown in FIGS. 2B and C comprised regions that are relatively distant from the tissue edge. Near the tissue edge, where the antibody concentration was highest and the epidermis had separated from the basement membrane, very strong labeling was seen uniformly along the lamina densa, at what had been the cell interface (FIG. 2D). Some label was seen still associated with the extracellular face of the hemidesmosome, but this was relatively rare (not shown).

Although the present inventors do not desire to be bound by theories and the limitations of scientific knowledge, the orientation of the molecular elements of the basement membrane zone seen by conventional microscopy may be entirely artifactual. Electron microscopic examination of rat incisor, tongue and gingiva prepared by rapid-freezing and freeze-substitution demonstrate a homogenous 25–100 nm thick electron-dense basement membrane completely lacking a lamina lucida (Goldberg et al., Eur. J. Cell Biol. 42:365–368 (1986)). One of the present inventors has made the same observation with the dermal-epidermal junction of human skin. Therefore, it is possible that the lamina lucida is an artifact resulting from the cell shrinking away from the basement membrane, and the lamina densa is the residue of the entire basement membrane. If this is the case, it is likely that kalinin is situated entirely within the basement membrane, with only one end concentrated at the site where the hemidesmosome contacts the basal lamina. The anchoring filaments would then reflect those species within the basal lamina that are strongly bound to the hemidesmosome and become taut and linear as they are pulled from the basement membrane as the cell shrinks away.

Kalinin Localization in Cell Cultures

Figure 3A:
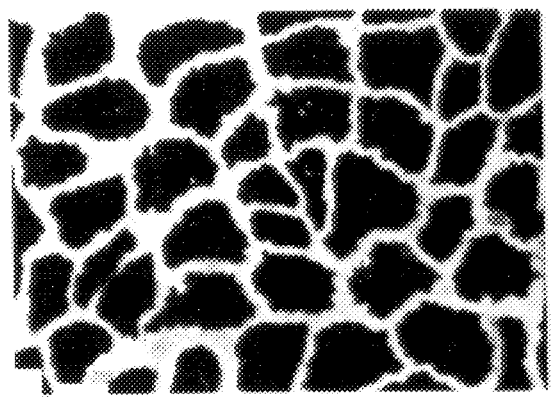
FIG. 3A is a photomicrograph of a confluent layer of cultured keratinocytes stained with monoclonal antibody BM165.
Figure 3B:
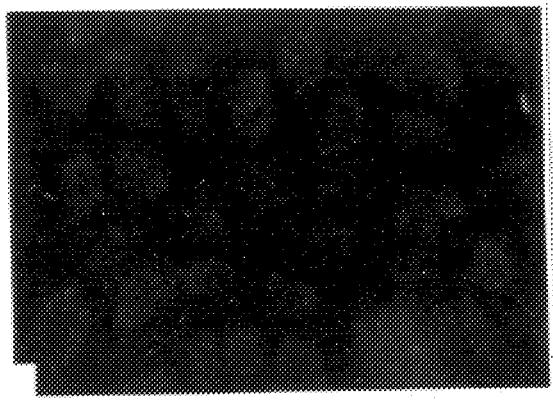
in FIG. 3B the culture was stained with control media.
Figure 3C:
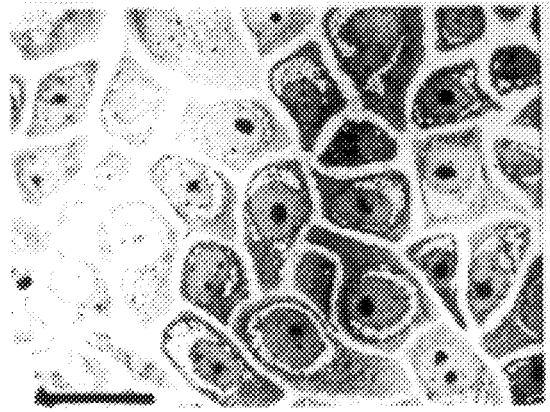
in FIG. 3C the transmission electron micrograph section is taken through the cell layer parallel to the culture substrate, the black bar indicating a length of 20 nm; and in FIG. 3D the cells are removed from the substrate with EDTA before staining with BM165.

The BM165 mAb was used to visualize the corresponding antigen in keratinocyte cultures. As shown in FIG. 3A, when applied to the top surface of a layer of confluent cells, the antibody localized to the surface of the plastic substrate between the cultured cells (compare to FIG. 3C, which is taken through the cell layer parallel to the culture substrate). No intracellular fluorescence was observed. This unusual localization could not be duplicated with antibodies to type-IV collagen (Sakai et al., Am. J. Pathology 108:310–318 (1982)), to laminin, or to type-VII collagen (Sakai et al., J. Cell Biol. 103:1577–1586 (1986)) (data not shown).

Figure 3D:

Such localization of BM165 mAbs was not observed when antibodies of the same immunological subtype, but of irrelevant specificity were used (data not shown). The antigen was also present on the substrate underneath the cells as shown by strong fluorescence of the entire plastic substrate after removal of the cells with 10 mM EDTA (FIG. 3D).

Figure 4A:
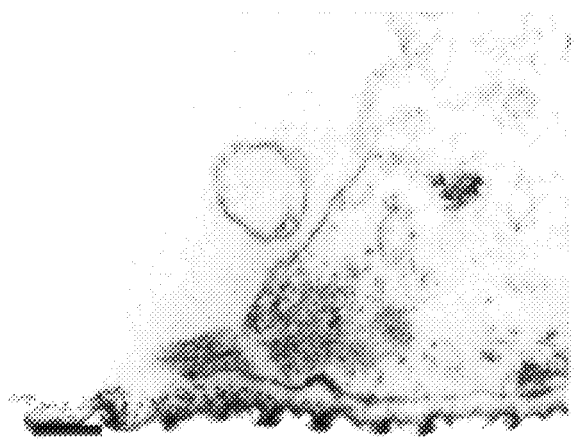
FIG. 4A is a photomicrograph of a continuous subcellular matrix in a keratinocyte culture that was grown to near confluency, then washed with PBS (phosphate-buffered saline) and incubated with BM165 monoclonal antibody followed by 5-nm gold-conjugated secondary antibody prior to fixation.
Figure 4B:
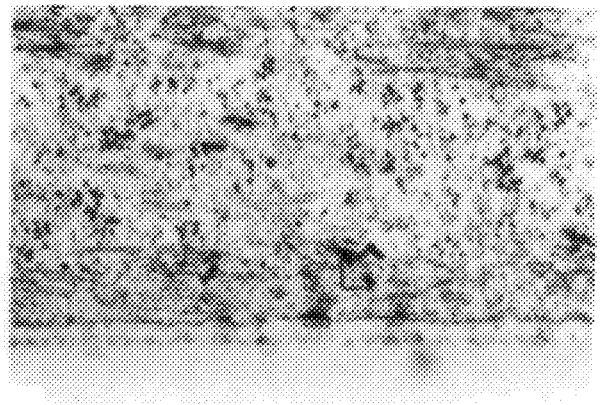
In FIG. 4B the keratinocytes were grown to near confluency and fixed immediately without staining with monoclonal antibody BM165.
Figure 4C:
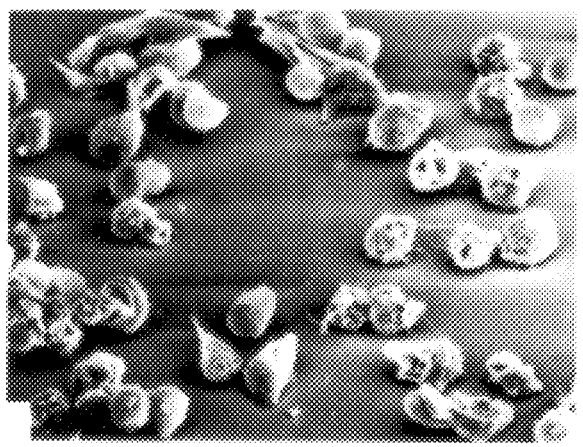

The BM165 antigen was also localized along a continuous subcellular matrix in keratinocyte cell culture, as shown in FIGS. 4A–4D. Keratinocytes were grown to near confluence and either fixed immediately (FIGS. 4B and 4D) or washed with PBS and incubated with BM165 mAb (50 μg/mL) followed by 5-nm gold-conjugated secondary antibody prior to fixation (FIGS. 4A and 4C). Electron microscopic examination of the antigen in keratinocyte cultures revealed a linear deposition of immunogold conjugates uniformly across the substrate upon a fine electron-dense feltwork (FIG. 4A). The feltwork continued under the cell, but was often unlabeled. Thickenings could occasionally be seen along the keratinocyte plasma membrane that resembled immature hemidesmosomes (FIG. 4B), similar to structures observed by others (Compton et al., *Lab. Invest.* 60:600–612 (1989)).

Figure 4D:
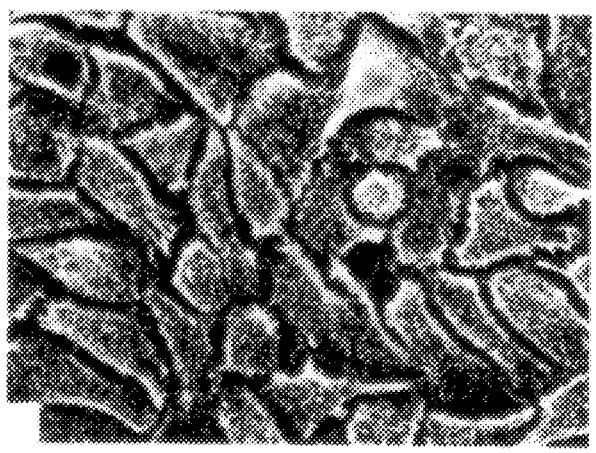
FIG. 4D is a scanning electron micrograph of a confluent culture prepared as in FIG. 4B.
Figure 5A:
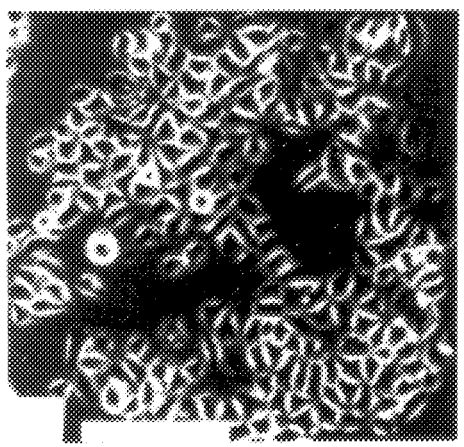
FIG. 5A is a photomicrograph of keratinocytes grown to 75–80% confluency, then washed and treated with PBS and photographed 10 minutes after treatment; the bar represents 20 µm.
Figure 5B:
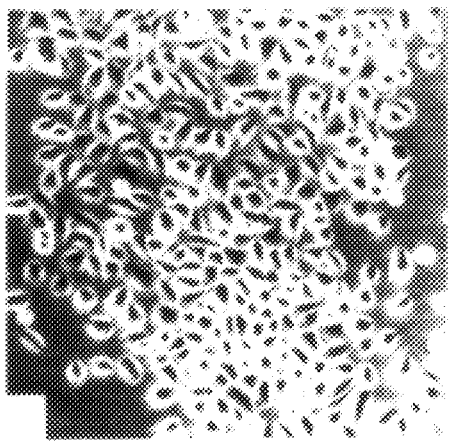
In FIG. 5B the cells were photomicrographed 60 minutes after PBS treatment.
Figure 5C:
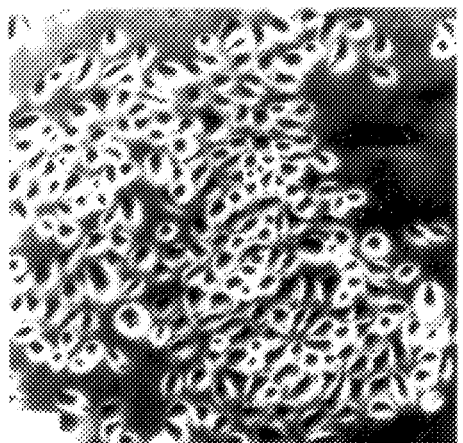
FIG. 5C is a photomicrograph similar to FIG. 5A in which the cells were washed with PBS and treated with 50 µg/mL BM165 mAb then photographed after 10 minutes.
Figure 5D:
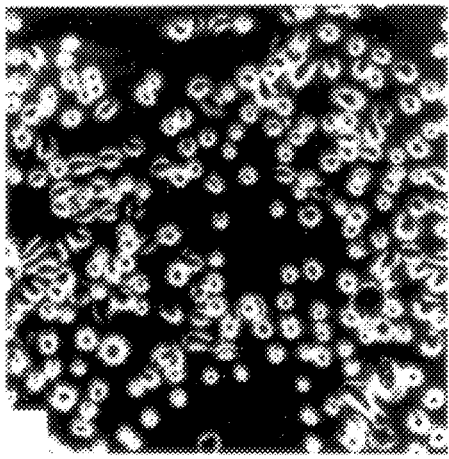
FIG. 5D shows the cells after 60 minutes.
Figure 5E:
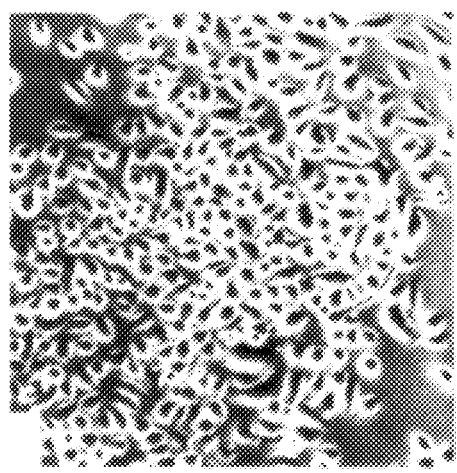
FIG. 5E is a photomicrograph similar to FIG. 5A in which the cells were washed with PBS and treated with 10 mM EDTA, photographed 10 minutes after treatment.
Figure 5F:
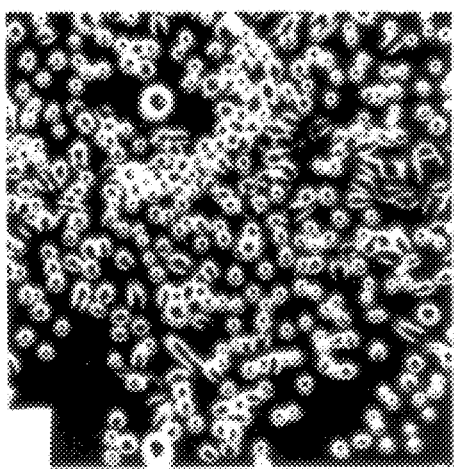
FIG. 5F shows them photographed after 60 minutes.

The ultrastructural immunolocalization studies of the BM165 antigen in keratinocyte cultures described above were complicated by a rounding and detachment behavior of the keratinocytes during long incubations with concentrated BM165 mAb. Scanning electron micrographs showing the altered morphology of the BM165 Mab-incubated cells compared to the morphology of untreated keratinocytes is shown in FIGS. 4C and 4D, respectively. The treated keratinocytes shown in FIG. 4C had become rounded and detached during incubation with the BM165 Mab.

Detached keratinocytes readily re-plated onto plastic and grew with equal vigor compared to untreated cells, indicating that the rounded and detached cells were not metabolically compromised by the antibody treatment (not shown).

To further pursue these observations, just-subconfluent keratinocyte cultures were separately incubated with purified BM165 mAb for 10 and 60 minutes. After incubation, the cultures were photographed (FIGS. 5A–F). Purified mAbs in PBS, PBS alone, or 10-mM EDTA were incubated with keratinocytes in parallel. Parallel cultures were also incubated with anti-type-VII monoclonal IgG in PBS for the corresponding same length of time. BM165 mAbs (FIGS. 5C and 5D) and EDTA (FIGS. 5E and 5F) were observed to cause extensive rounding and detachment of the keratinocytes after 60 minutes' incubation. Such rounding and detachment were not observed when the cultures were incubated with PBS (FIGS. 5A and 5B), anti-type-VIII collagen nor anti-laminin (not shown). Dermal fibroblasts were rounded and detached by EDTA but not by BM165 Mab (not shown). Therefore, the BM165 epitope is involved in keratinocyte attachment, but not in the attachment of dermal fibroblasts to substrates.

The photomicrographs in FIG. 3A also indicate that confluent keratinocyte cultures exhibit no intracellular fluorescence. To evaluate substrate deposition of the antigen occurring relative to the time of plating, keratinocytes were plated at low density, and the development of fluorescence was observed as a function of increasing cell density.

Figure 6A:
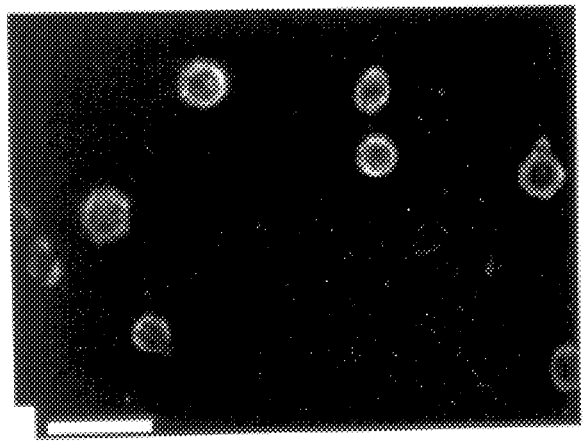
FIG. 6A is a photomicrograph of cultured keratinocytes that were exposed to the BM165 monoclonal antibody after 6 hours in culture, FIG. 6B after 24 hours in culture, and FIG. 6C after 48 hours in culture.
Figure 6B:
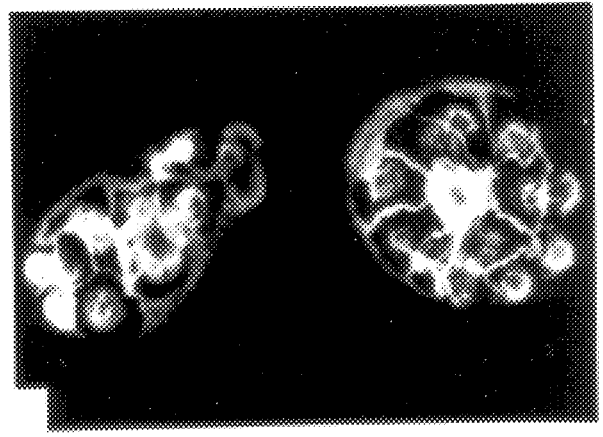
FIGS. 6D and 6E are photomicrographs similar to FIG. 6B illustrating substrate labeling along the paths of migrating keratinocytes.
Figure 6C:
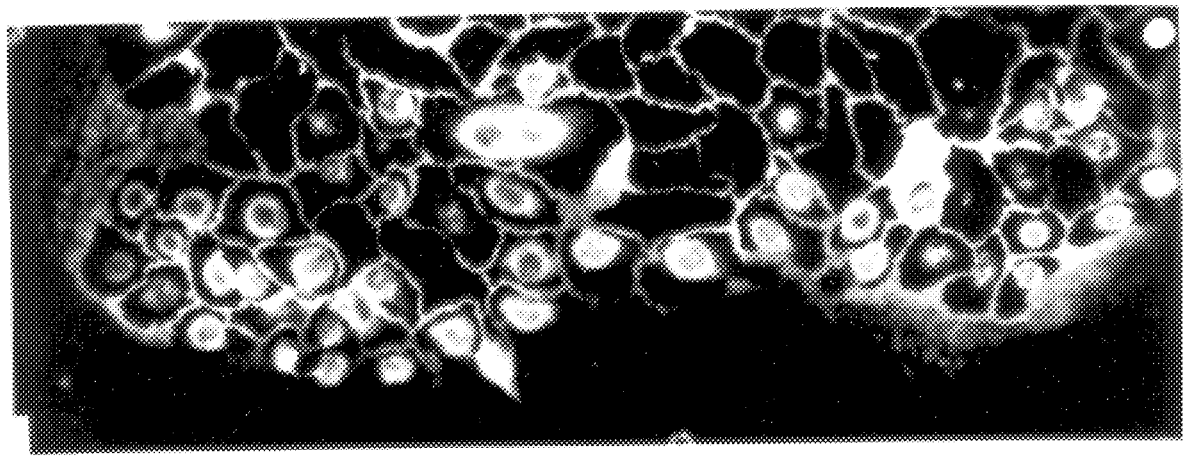
Figure 6D:
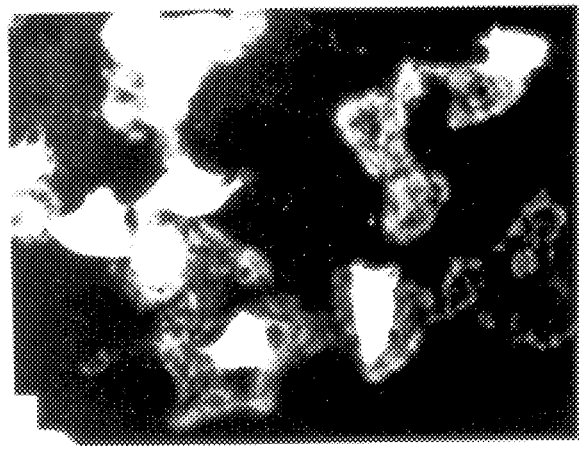
Figure 6E:
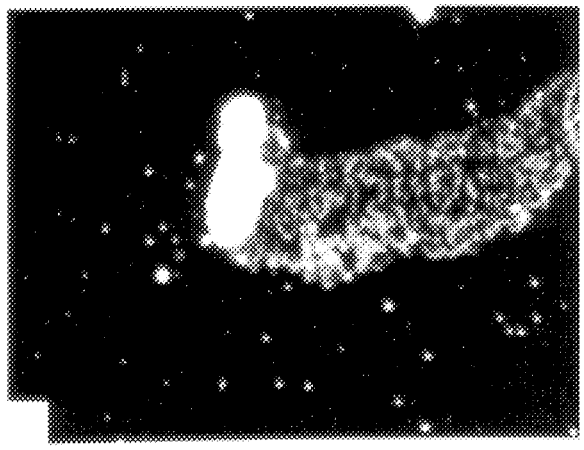

Photomicrographic results of these studies are shown in FIGS. 6A–6E, and demonstrate that synthesis of the BM165 antigen correlated with growing and migrating cells. At six hours after plating, only intracellular fluorescence was observed (FIG. 6A). By 24 hours, individual cells and cell clusters exhibited both perinuclear intracellular fluorescence and fluorescent staining of the substrate immediately adjacent the cells (FIGS. 6B, 6D and 6E). In some cases, cells appeared to have migrated, leaving behind fluorescent stain attached to the substrate (FIGS. 6D and 6E). As the cell clusters enlarged (FIG. 6C), only the peripheral cells demonstrated intracellular fluorescence, showing that cells situated in the center regions of the clusters were no longer synthesizing this antigen. These results are consistent with previous observations that cell growth and migration occur at the periphery of keratinocyte colonies and internal cells are quiescent (Barrandon et al., *Cell* 50:1131–1137 (1987)). Since the interior cells of confluent cultures did not appear to synthesize the BM165 antigen, we concluded that the BM165 antigen is produced primarily by growing and migrating cells.

These data show that, in developing or regenerating epithelia, kalinin is initially distributed. uniformly upon the migration substrate. This is supported by the observation that keratinocytes cultured either on plastic or glass deposit kalinin uniformly upon the substrate, not solely beneath what appear in culture to be immature hemidesmosomes. Once cultures of keratinocytes have become confluent and have a sufficient surface to be grafted on a patient, the confluent culture has stopped depositing kalinin on the substrate. This is believed to account for the poor adhesion of cultured keratinocytes to the dermis, muscle or subcutaneous tissue of a skin graft site. The use of enzymes such as dispase or trypsin to remove keratinocytes from a culture surface may also degrade the kalinin. Hence, supplying exogenous kalinin after enzyme removal of the keratinocyte can offset the damage caused by use of the enzyme.

PAGE of Kalinin

Figure 7:
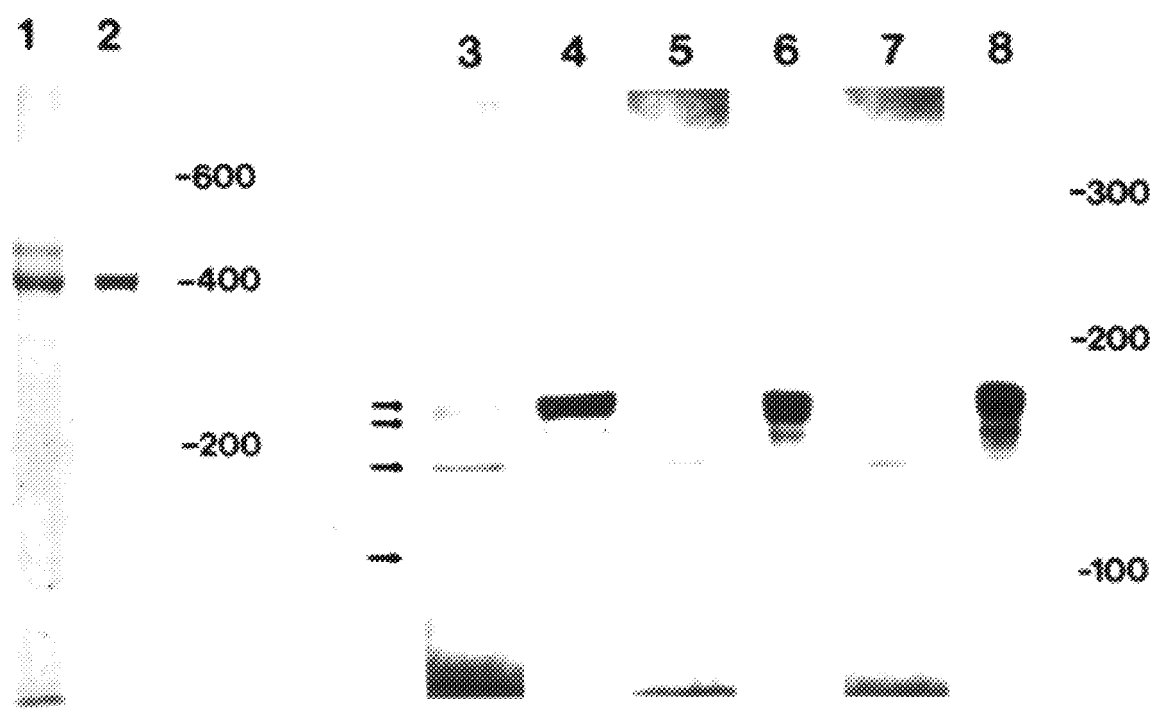
FIG. 7 is a western blot showing an electrophoretic analysis of the BM165 antigen isolated from keratinocyte culture medium.

To further characterize the antigen, the BM165 immunogen was fractionated from keratinocyte medium by immunoaffinity chromatography using BM165 mAbs, and was analyzed by polyacrylamide gel electrophoresis (FIG. 7). As described above (see, Affinity Purification of the BM165 Antigen), the BM165 antigen was affinity-purified from spent keratinocyte culture medium. When analyzed by sodium dodecyl sulfate-polyacrylamide gel electrophoresis (SDS-PAGE) before disulfide reduction, two species were visualized by staining with Coomassie Blue (lane 1). Both molecular species were immunoblot positive (lane 2). The predominant species migrated with an estimated $M_r$ of approximately 410,000 daltons, and a minor species of $M_r$ 460,000 daltons was often seen.

After disulfide bond reduction with mercaptoethanol, four major electrophoretic species were resolved (lane 3, arrows): $M_r$=165,000, 155,000, 140,000 and 105,000 daltons. None of these bands were immunoreactive with polyclonal antiserum to EHS laminin (Sigma), or with monoclonal antibodies to human A, B1 or B2 chains (Engvall) (data not shown). Only the 165-kDa (kilodalton) species (and an immunoreactive smaller species that does not correspond to any of the chemically stained bands and is presumed to be a degradation product) contains the BM165 epitope as shown by western blot when probed with mAb BM165 (lane 4).

The disulfide bonded 410-kDa and 460-kDa species were separately excised from the gel and reduced with 2-mercaptoethanol. The reduction products were separated by electrophoresis. The 460-kDa species included the 165-kDa, 155-kDa and 140-kDa chains (lane 5) and a small amount of a 200-kDa species seen only faintly after staining with Coomassie blue (lane 3). The 200-kDa species also included the BM165 epitope. The 460-kDa species included the 165-kDa, 140-kDa and 105-kDa chains (lane 7). These results are consistent with identification of a protein molecule having three non-identical chains.

The differences in the electrophoretic mobilities of the non-reduced species can be explained by a conversion of the 155-kDa species to a 105-kDa species by proteolysis.

The results also showed that the 200-kDa and 165-kDa chains bear a precursor-product relationship, as confirmed by biosynthetic pulse-chase experiments.

Rotary Shadowing of Kalinin

Figure 8A:
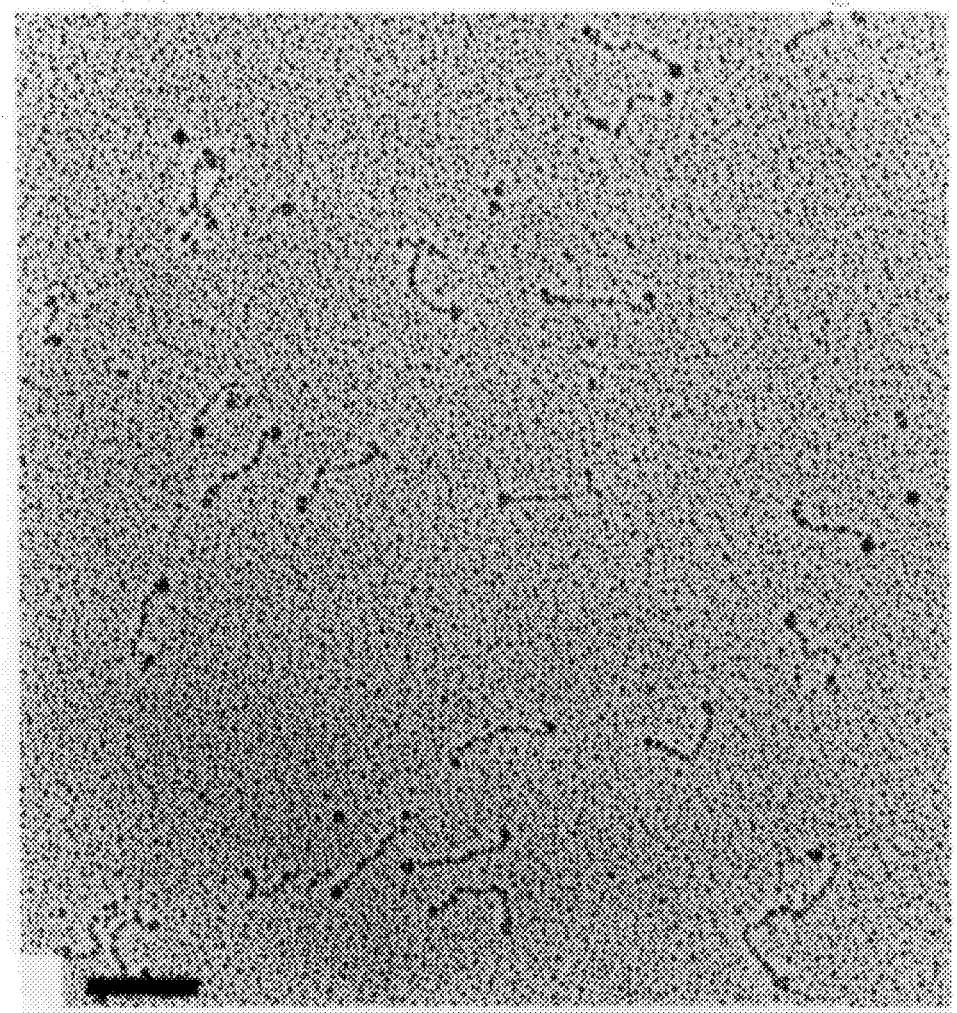
Figure 8B:
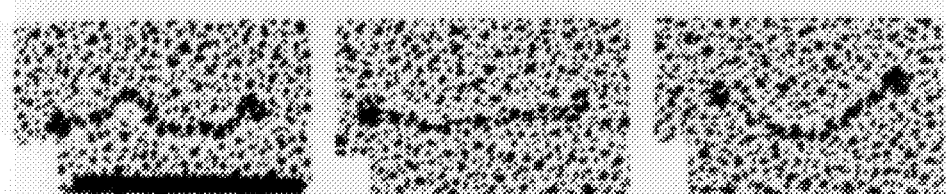
Figure 8C:
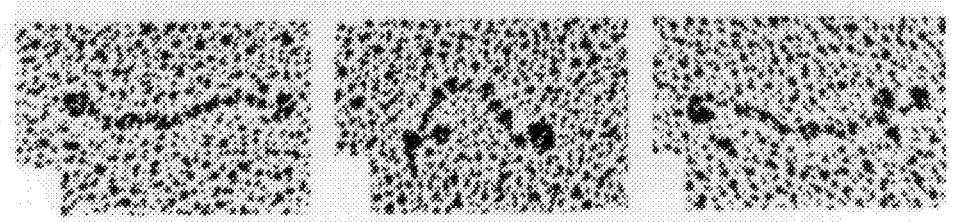

Rotary-shadow imaging of the purified BM165 antigen revealed a linear molecule comprising a central rod 107 nm long (FIG. 8A). The molecule is seen in two forms. The more common form appears to have an extended dumbbell-shaped profile (FIG. 8B, 8C and 8I) with a globular knob at each terminus of the rod. One knob often appears smaller than the other. The lesser abundant form is asymmetric, with a large globule at one end and two smaller globules at the other (FIGS. 8E, 8F and 8G). Both forms are different from any other molecules of which the inventors are aware The relative abundance of the two forms, and the presence of an additional knob on the larger species, is consistent with the larger image being representative of the 460-kDa form.

Rotary shadowing of kalinin indicates that it is an asymmetric molecule. This confirmation is consistent with a molecular structure in which one site on kalinin molecules is capable of interaction with receptors on the keratinocyte surface and another part remains buried within the lamina densa, thus providing cell-substrate adhesion. This impression is further supported by the observed disruption of cell-substrate contact upon incubation of cultured cells with the antibody, and the consistent and dramatic de-epithelization of skin caused by the BM165 antibody.

Precursor-Product Relationships of Kalinin

A high-molecular-weight (HMW) form of kalinin is secreted by keratinocytes and is processed extracellularly to lower-molecular-weight forms. The extracellular processing appears to involve two independent steps. These processing steps, and the products they produce, are more fully described in applicants' co-pending U.S. patent application Ser. No. 07/936,850 filed Aug. 28, 1992, now U.S. Pat. No. 5,352,668, which is incorporated herein by reference.

K-Laminin Variant

The present inventors have found that a subset of epithelial basement membranes contain a novel variant form of laminin, in addition to laminin of the EHS prototype. Skin in organ culture and epidermal cells in primary culture produce the variant, which has a "Y" shaped rotary shadowed image. This variant is composed of a B1 chain, a B2 chain, and a third 190 kDa chain which is immunologically distinct from the laminin A chain but immunologically and structurally related to the 200/165 kDa subunit of kalinin. As used herein, the term "K-laminin" refers to this variant, that is more fully described below.

Material for K-Laminin Isolation

Keratinocyte growth medium (KGM) was purchased from Clonetics Corporation, San Diego, Calif. Hydrocortisone, cholera toxin, and tissue culture grade epidermal growth factor were purchased from Sigma Chemical Company, St. Louis, Mo. Mouse EHS laminin, DME, heat inactivated FBS, Ham's F-12 nutrient mixture, and penicillin/streptomycin 100×solution were purchased from Gibco/BRL, Grand Island, N.Y. Rabbit anti-mouse IgG immunobeads, goat anti-rabbit IgG immunobeads, and prestained high molecular weight markers for electrophoresis were purchased from Biorad, Richmond, Calif. CNBr activated sepharose C1-4B beads were purchased from Pharmacia/LKB, Pleasant Hill, Calif. V8 protease was purchased from ICN/Flow, Irvine, Calif. 35S-cysteine and 35S-methionine were purchased from Amersham, Danvers, Mass.

Methods for K-Laminin Isolation

Antibodies

The mAb BM165 reacts with the 165 kDa chain of kalinin, as previously described herein and in Rousselle et al., *J. Cell Biol.* 114:567–576 (1991), which is incorporated by reference. Preparation and specificity of mAb K140 which reacts with the 140 kDa subunit of kalinin and rabbit polyclonal antiserum against kalinin is described below. The laminin A chain specific mAbs 1F5, 11D5 (Engvall, et al., *Cell Regul.* 1:731–740 (1990); 4C7, Engvall et al., *J. Cell Biol.* 103:2457–2465 (1986); laminin B2 chain specific mAb 2E8, Engvall et al., *J. Cell Biol.* 103:2457–2465 (1986); and anti merosin mAb 5H2, Leivo et al., *Lab. Invest.* 60:783–790 (1989)) were provided by Dr. Eva Engvall of the La Jolla Cancer Research Foundation. Affinity purified polyclonal antibody against mouse laminin was obtained from Sigma Chemical Company, St. Louis, Mo. Monoclonal antibodies were purified from hybridoma medium as previously described (Keene et al., 1991). All the publications in this paragraph are incorporated by reference to provide further disclosure of the method of preparation of these antibodies.

During the course of these studies a new mAb, 545, was developed. Antigen for mAb 545 was obtained from the reduced product of the PF3 fraction of human amniotic membrane prepared as previously described (Maddox et al., *J. Biol. Chem.* 261:21381–21385 (1989)). Briefly, disulfide bonds of the PF3 fraction were reduced and alkylated with vinyl pyridine. Peptides containing cysteine residues were reduced in 100 fold molar excess of 2-mercaptoethanol overnight at room temperature in 0.5M TrisHCl buffer, pH 7.5, containing 0.2M NaCl and 5 mM EDTA. Equimolar amounts of vinyl pyridine to mercaptoethanol were added and after a further 90 minute incubation at room temperature, the peptides were separated from excess reagent by gel filtration, and utilized for immunization of a BALB/c mouse as previously described (Sakai et al.,*J. Cell Biol.* 103:1577–1586 (1986)). Mab 545 has been shown to specifically immunoprecipitate laminin from a complex mixture of proteins in radiolabeled keratinocyte conditioned medium (not shown). Additionally, this antibody has been shown to have a staining pattern identical to polyclonal anti-laminin antibody on human skin sections by indirect immunofluorescent microscopy (not shown).

Immunogen necessary to prepare "K140" mabs was purified from human amnion. Collagenase-extracted human amnionic membranes were processed by a procedure adapted from Bächinger et al., *J. Biol. Chem.* 256:10095–10101 (1990). Proteins were precipitated from the initial soluble fraction by the addition of ammonium sulfate to a final concentration of 30% (w/v) and incubated overnight at 4° C. Precipitated materials were recovered following centrifugation (17,000×g, 60 minutes) and resuspended in chromatography buffer prior to dialysis, which greatly decreased the overall viscosity of the sample, presumably due to the removal of nucleic acids. Remaining insoluble material was removed from the sample by ultracentrifugation (18,000 rpm, 1 hour) in a Beckman Type 19 rotor. The resulting immunogen was used to inoculate two Balb/C mice. Hybridomas were prepared and screened initially by indirect immunofluorescent microscopy according to Sakai et al., *J. Cell Biol. 103:1577–15865* (1986). One hybridoma named "K140" produced a mAb that specifically recognized the 140-kDa subunit of kalinin.

Cell culture

Keratinocytes were cultured from newborn foreskins by a modification of an established method (Rheinwald and Green, *Cell* 6:331–334 (1975); O'Keefe et al., *J. Invest. Dermatol.* 90:767–770 (1988)). Prior to the first passage cultures were incubated in sterile PBS containing 0.02% EDTA for 5 minutes, gently pipetted to remove dermal fibroblasts and 3T3 cells, then washed and treated with trypsin 0.05% and EDTA 0.02% w/v to suspend keratinocytes. Subsequently, cells were grown in KGM containing 0.15 mM CaCl$_2$ and subcultured according to the manufacturer's instructions. Squamous cell carcinoma line SCC-25 (deposited with ATCC of Rockville, Md. under accession no. CRL 1628) was cultured in 50% Ham's F-12 medium, 50% DME medium, with 0.5 µg/ml hydrocortisone, and 10% FBS, and was routinely subcultured with 0.05% trypsin, 0.02% EDTA in PBS.

Kalinin was also obtained from SCC-25 squamous cell carcinoma cells (ATCC # CRL1628). Cell-associated kalinin was obtained from 80-percent confluent cultures of SCC-25 cells grown on 100-mm diameter plastic culture dishes. The cell layers were washed with PBS, then extracted with ice-cold lysis buffer (10-mM Tris-HCl pH 7.4, 150-mM NaCl, 2-mM EDTA, 250-µM PMSF, 1 mM n-ethylmaleimide, 0.3% NP-40, 0.05% Triton X100, 0.3% sodium deoxycholate, 0.1% BSA, and 0.1% SDS). All subsequent steps were performed at 4° C. Cells and matrix were removed from the dishes using a cell lifter, then solubilized with a Dounce homogenizer and centrifuged at 25,000×g for 30 minutes. The supernatant was treated with diisopropyl fluorophosphate (5 µg/mL), combined with K140-Sepharose, and incubated overnight on a rocking platform. The matrix was transferred to a chromatography column, washed with 50 column volumes of lysis buffer, then 50 column volumes of PBS. The column was then eluted with 1-M acetic acid. Peak fractions were determined by UV absorbance at 280 nm, pooled, dialyzed against water, then lyophilized.

Cell labeling

For 24 hour labeling experiments, dissociated third passage keratinocytes were allowed to attach to tissue culture plastic dishes, 5×105 cells/cm$^2$, in complete KGM for 2 hours. Adherent cells were briefly washed with methionine and cysteine deficient KGM. Labeling was performed in deficient KGM containing 50 µCi/ml each of 35S-methionine and 35S-cysteine for 24 hours under standard culture conditions.

In organ culture experiments, fetal bovine skin was removed from a 10 inch (crown to rump length) calf less that four hours out of the uterus. Skin was cut into 1 mm×1 mm sections and cultured in suspension for 24 hours in methionine and cysteine deficient DME containing hydrocortisone (0.5 µg/ml) cholera toxin (10 ng/ml), epidermal growth factor (10 ng/ml), penicillin (100 units/ml), streptomycin (100 µg/ml) fetal bovine serum 2% 35, S-methionine (50 µCi/ml), and 35S-cysteine (50 µCi/ml). Subsequently, tissue was washed and incubated in complete nonradioactive DME containing the above factors and 10% FBS for 72 hours. Aliquots of tissue were removed after the 24 hour labeling period and again after the 72 hour nonradioactive chase period and processed for immunoprecipitation as described below for cell samples.

Antibody precomplexing and radioimmunoprecipitation

For each sample to be analyzed 10 µg protein-G purified monoclonal antibody was added to 100 µl rabbit anti-mouse IgG immunobeads or 10 µl polyclonal rabbit antisera was added to 400 µl "second antibody" goat anti-rabbit IgG immunobeads. For polyclonal control conditions 10 µl normal rabbit serum was used. For monoclonal control conditions, no primary antibody was used. The mixtures were incubated at 37° C. for two hours with mild agitation. The antibody-immunobead complexes were pelleted by centrifugation at 2500 rpm, washed once with radioimmunoprecipitation assay (RIPA) buffer (10 mM Tris-HCl pH 7.4, 150 mM NaCl, 2 mM EDTA, 250 µM PMSF, 1 mM n-ethyl maleimide, 2 mM 1methionine, 2 mM 1-cysteine, 0.3% NP-40, 0.05% triton X-100, 0.3% sodium deoxycholate, 0.1% BSA), and repelleted prior to use with labeled sample.

Cell layers were washed once with nonradioactive culture medium then harvested with a cell scraper and ice cold RIPA buffer containing 0.1% SDS. All subsequent steps were performed at 40° C. Labeled cell material was solubilized in a Dounce homogenizer and spun at 14,000 rpm for 10 minutes. Labeled medium was removed from culture and centrifuged at 2000 rpm. Preclearing of each sample was accomplished by adding aliquots of labeled cell or medium supernatants to the centrifuged pellets of either 400 µl goat anti-rabbit IgG immunobeads precomplexed with 10 µl nonimmune rabbit serum, or 100 µl rabbit anti-mouse IgG immunobeads. Each sample was vortexed briefly, then left on a rocking platform for 1 hour. The mixture was then centrifuged at 14,000 rpm for 10 minutes, and the supernatant combined with the centrifuged pellet of immunobeads precomplexed with specific antibody. Each sample was incubated with specific antibody for 18 hours on a rocking platform, then pelleted by centrifugation at 2500 rpm for 10 minutes. After centrifugation, the supernatant was removed and the pellet was washed with RIPA buffer (medium samples) or RIPA buffer containing 0.1% SDS (cells), briefly vortexed, then recentrifuged. After five washes, the pellets were mixed with sample buffer, heated to 95° C. for 3 minutes, recentrifuged, and the supernatant was analyzed by SDS-PAGE. In one experiment, kalinin was removed from precleared labeled keratinocyte medium by passage over a mAb K140-sepharose column prior to immunoprecipitation with mAb BM165.

Immunoaffinity purification of the laminin variant

Human amniotic fluid obtained from first and second trimester amniocentesis or squamous cell carcinoma conditioned medium were each centrifuged at 1000 rpm to remove cell debris. Supernatants were brought to 250 µm PMSF, 1 mM n-ethylmaleimide, 2 mM EDTA, and 0.02% sodium azide, then centrifuged at 18,000 rpm for 90 minutes. The supernatants were then passed over either mAb BM165-sepharose (Rousselle et al., *J. Cell Biol.* 114:567–576 (1991), or mAb 2E8-sepharose columns (1 mg antibody per ml matrix, coupled to CL4B sepharose per manufacturer's instructions, Pharmacia, Pleasant Hill, Calif.), washed with 50 column volumes PBS, then eluted with 1 M acetic acid. Peak fractions were determined by W 280 absorbance and western blotting, treated with diisopropyl fluorophosphate (5 µg/ml), and dialyzed against water. Samples for rotary shadowing analysis were dialyzed against 0.2M ammonium bicarbonate and concentrated 5 fold on a centricon-30 microconcentrator (Amicon, Danvers, Mass).

Other methods

The following procedures were performed as previously described: SDS-PAGE electrophoresis (Laemmli *Nature* 277:680–685 (1970)), electrophoretic transfer of proteins to nitrocellulose with immunoblot analysis (Lunstrum et al., *J. Biol. Chem.* 261:9042–9048 (1986)), visualization of rotary shadowed images by electron microscopy (Morris et al., *J. Biol. Chem.* 261:5638–5644 (1986)), indirect immunofluorescent microscopy of frozen sections of human tissue (Sakai et al., *J. Cell Biol.* 103:1577–1586 (1986)), fluorography of acrylamide gels containing radioactive proteins (Bonner and Laskey, *Eur. J. Biochem.* 46:83–88 (1974)), and V8 protease digestion of excised gel bands (Cleveland et al., *J. Biol. Chem.* 252:1102–1106 (1977)).

K-Laminin Characterization

Figure 10:
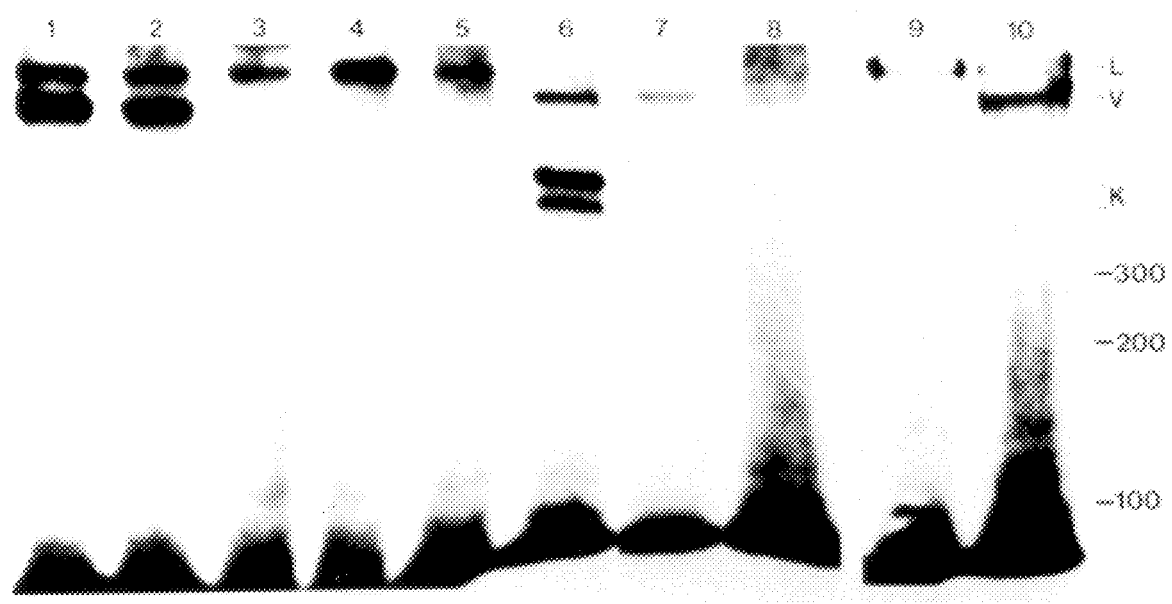
FIG. 10 is an SDS-PAGE gel that shows the result of a nonreduced immunoprecipitation of keratinocyte medium using antibodies to visualize laminin (L), k-laminin variant (V), and kalinin (K).

Human keratinocyte conditioned medium derived from a 24 hour radiolabeling period was immunoprecipitated with the following antibodies as shown in FIG. 10: lane 1, polyclonal anti-laminin; lane 2, 2E8 (monoclonal anti-laminin B2 chain): lane 3, 1F5 (monoclonal anti-laminin A chain, from hybridoma ATCC Accession No. HB 9645, deposited Feb. 12, 1988, with the American Type Culture Collection, Rockville, Md.); lane 4, 4C7 (monoclonal anti-laminin A chain); lane 5, 11D5 (monoclonal anti-laminin A chain); lane 6, BM165 (monoclonal anti-kalinin 200/165 kDa chain); lane 7, BM 165 immunoprecipitation of medium which has been cleared of kalinin by mAb140 (monoclonal anti-kalinin 140 kDa chain); lane 8, control (no primary antibody); lanes 9 and 10, medium sequentially immunoprecipitated, first with 4C7 monoclonal anti-laminin A chain (lane 9) then with polyclonal anti-laminin (lane 10). Samples were analyzed by SDS-PAGE on 3–5% acrylamide gels and visualized by autoradiography. In FIG. 10, L=laminin, V=variant, K=kalinin, and the right margin indicates Mr×10$^{-3}$.

Polyclonal anti-EHS laminin specifically precipitates two electrophoretic species prior to disulfide bond reduction (FIG. 10, lane 1). No bands are precipitated from the same medium in the absence of primary antibody (lane 8). The same two electrophoretic species are precipitated by monoclonal anti-laminin B2 chain antibody 2E8 (lane 2). In contrast, monoclonal anti-laminin A chain antibodies 1F5, 4C7 and 11D5, precipitate only the slower electrophoretic species (lane 3, 4 and 5, respectively). MAb BM165 coprecipitates kalinin and the faster migrating species (lane 6). The mAb K140 precipitates kalinin but not the laminin variant from labeled keratinocyte medium (not shown). When kalinin is precleared from labeled medium with an excess of K140, BM165 mAb only precipitates the faster migrating laminin variant (lane 7).

Given the characterized specificity of the immunological reagents, the results suggest that human keratinocytes secrete a lower molecular weight variant of laminin containing at least a B2 chain, but not a normal A chain. These results also show that mAb BM165 cross reacts with the faster migrating laminin species, suggesting that immunologically the variant chain contained in this laminin species is more closely related to the kalinin 200/165 kDa chain than to the laminin A chain. Anti-merosin mAb 5H2 failed to precipitate either species from keratinocyte medium (not shown) consistent with the absence of merosin from the dermal-epidermal basement membrane of human skin.

To further verify the identity of the faster electrophoretic species as a laminin variant, radiolabeled keratinocyte medium was precleared of normal laminin using anti-laminin A chain antibody and then reprecipitated using polyclonal anti-laminin serum. The anti-A chain antibody removes only laminin, leaving the variant which is specifically removed by the polyclonal serum plus a small amount of conventional laminin (lanes 9,10).

Figure 11:
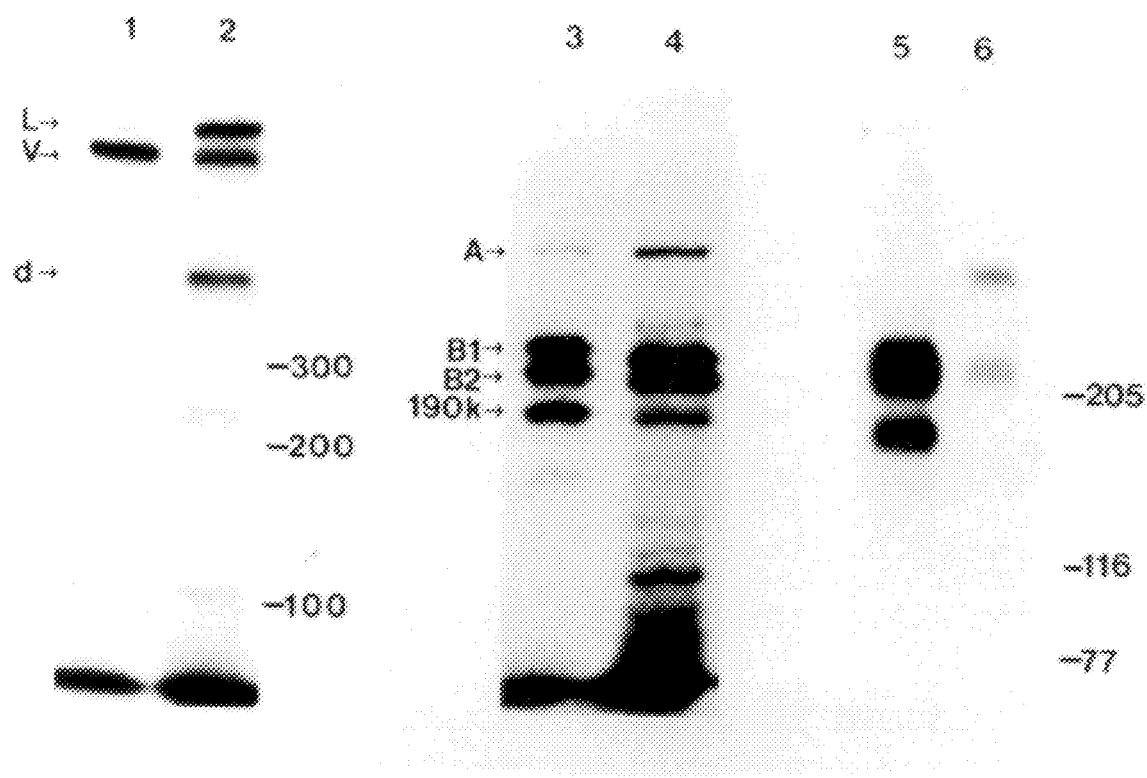
FIG. 11 is an SDS-PAGE gel that compares laminin in keratinocyte cell and medium fractions following a 24 hour metabolic labeling period.

Comparison of laminin keratinocyte cell and medium fractions is shown in FIG. 11. Following a 24 hour metabolic labeling period, keratinocyte conditioned medium (lanes 1,3) and keratinocyte cell fraction (lanes 2, 4) were each immunoprecipitated with polyclonal anti-laminin Precipitated materials were then separated by nonreduced SDS-PAGE on a 3–5% gradient gel (lanes 1,2) and separated by reduced SDS-PAGE on 5% acrylamide gel (lanes 3.4). Nonreduced gel bands containing the variant (V, lane 1) and laminin (L, lane 1) were excised from the dried gel, rehydrated with sample buffer containing 2% 2-mercaptoethanol, and separated by second dimension SDS-PAGE on a 5% acrylamide gel. The variant band is lane 5 and the laminin band is lane 6. All samples were visualized by fluorography.

When the anti-laminin immunoprecipitation product from keratinocyte medium fractions (FIG. 14A, lane 1) is compared with that of keratinocyte cell fractions (lane 2) by nonreduced SDS-PAGE, it is apparent that after a 24 hour labeling period, there is a greater fraction of laminin (FIG. 11, L) present in the cell fraction, than in the medium fraction. The cell fraction also contains a strong 400 kDa band (FIG. 11, d) which reduces to a pair of bands at 220–210 kDa (not shown). This 400 kDa band is therefore interpreted to be a B1–B2 chain dimer, whose existence has been previously proposed (Cooper et al., *Eur. J. Biochem.* 119:189–197 (1981); Morita et al., *Biochem. J.* 229:259–264 (1985); Peters et al., *J. Biol. Chem.* 260:14732–14742 (1985)). No laminin A chain was detected in the second dimension analysis of the 400 kDa band (not shown). Reduction of the medium derived immunoprecipitate (lane 1) clearly shows the predominance of bands in the positions of the laminin B1 and B2 chains, and in the 190 kDa position (lane 3).

Consistent with the presence of a minor amount of laminin, only small amounts of laminin A chain are seen. In contrast, reduction of the cell derived materials (lane 4) shows amounts of A, B1, B2 and 190 kDa chains expected from a nearly equal mixture of laminin and the variant indicated by the unreduced gel pattern (lane 2). When the nonreduced variant gel band (FIG. 11, lane 1 band V) is excised and analyzed by SDS-PAGE following disulfide bond reduction (FIG. 11, lane 5), a broad band containing the B chains and a distinct 190 kDa band are present. Alternatively, when the nonreduced laminin gel band is similarly treated, a 400 kDa A chain and no 190 kDa band are observed (lane 6). Together with the results presented in FIG. 6, these data indicate that the variant does contain chains electrophoretically identical to both the B1 and B2 chains, and contains a third chain of 190 kDa that is not immunoreactive with three monoclonal antibodies each directed toward different epitopes within the A chain, but which is reactive to a monoclonal antibody directed against the 200/165 kDa subunit of kalinin.

Figure 12:
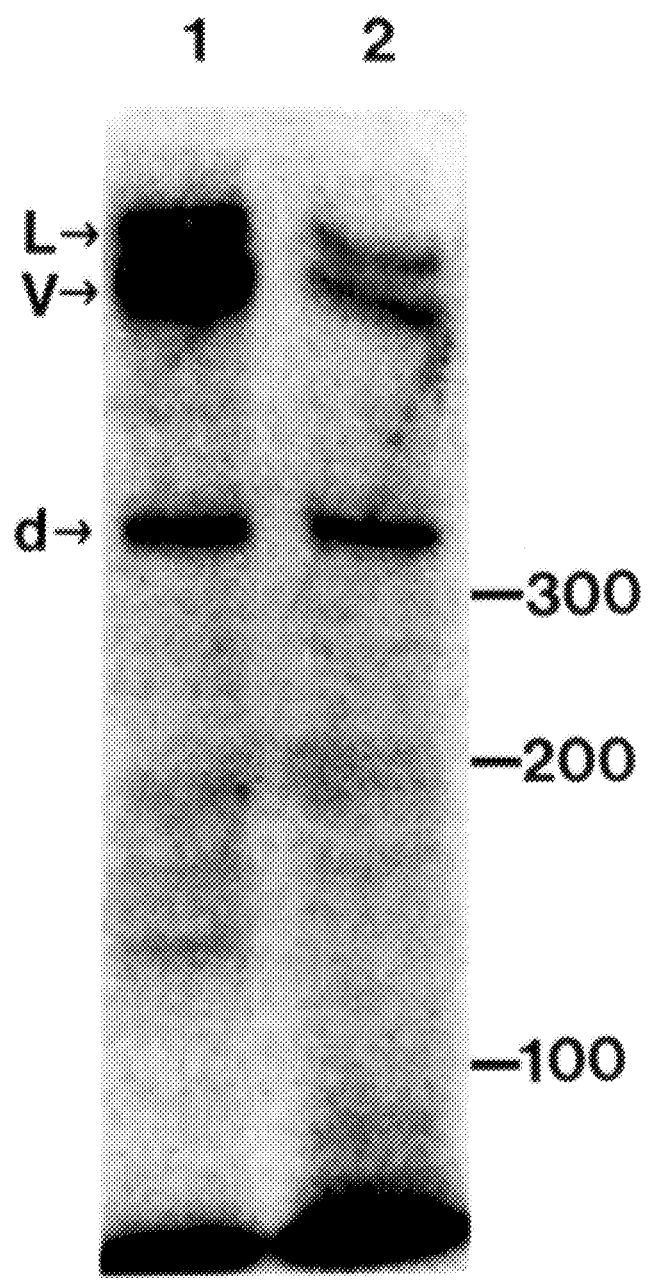
FIG. 12 is an SDS-PAGE that autoradiographically visualizes laminin (L), the k-laminin variant (V), and a B1, B2 dimer (d).

Laminin biosynthesis in skin organ culture was studied by suspending fetal bovine skin in culture for metabolic labelling for 24 hours. Analysis was either performed immediately (FIG. 12, lane 1) or after an additional 72 hour period of culture in nonradioactive medium (lane 2). Samples were immunoprecipitated with polyclonal anti-laminin antibody, separated by nonreduced SDS-PAGE on a 3–5% acrylamide gel, then visualized by autoradiography. In FIG. 12, L=laminin, V=variant, and d=dimer.

These organ culture studies with fetal bovine skin reveal that after a 24 hour labeling period, the nonreduced pattern of materials immunoprecipitated with polyclonal laminin antisera from cultured skin (FIG. 12, lane 1) is similar to that obtained from 24 hour labeled keratinocyte cell fractions (FIG. 11, lane 2). This finding indicates that production of the variant species is not an artifact of primary cell culture and production also occurs in skin organ culture. When the labeled skin is cultured in nonradioactive medium for an additional 72 hours there is a diminution of the intensity of the laminin and variant species but there is no significant loss of intensity of the presumed B1–B2 dimer (FIG. 3, lane 2). Although there is a diminution of the intensity of the bands representing the variant and laminin, indicating turnover or increased insolubilization of these materials to assay procedures, there is no evidence of one form being processed into the other. The preserved intensity of the B1–B2 dimer band after a period of nonradioactive chase suggests that the dimer may not simply represent incompletely disulfide bonded laminin, but that it may represent a stable entity that is sequestered for future use either in the assembly of laminin or for some other purpose.

Figure 13A:
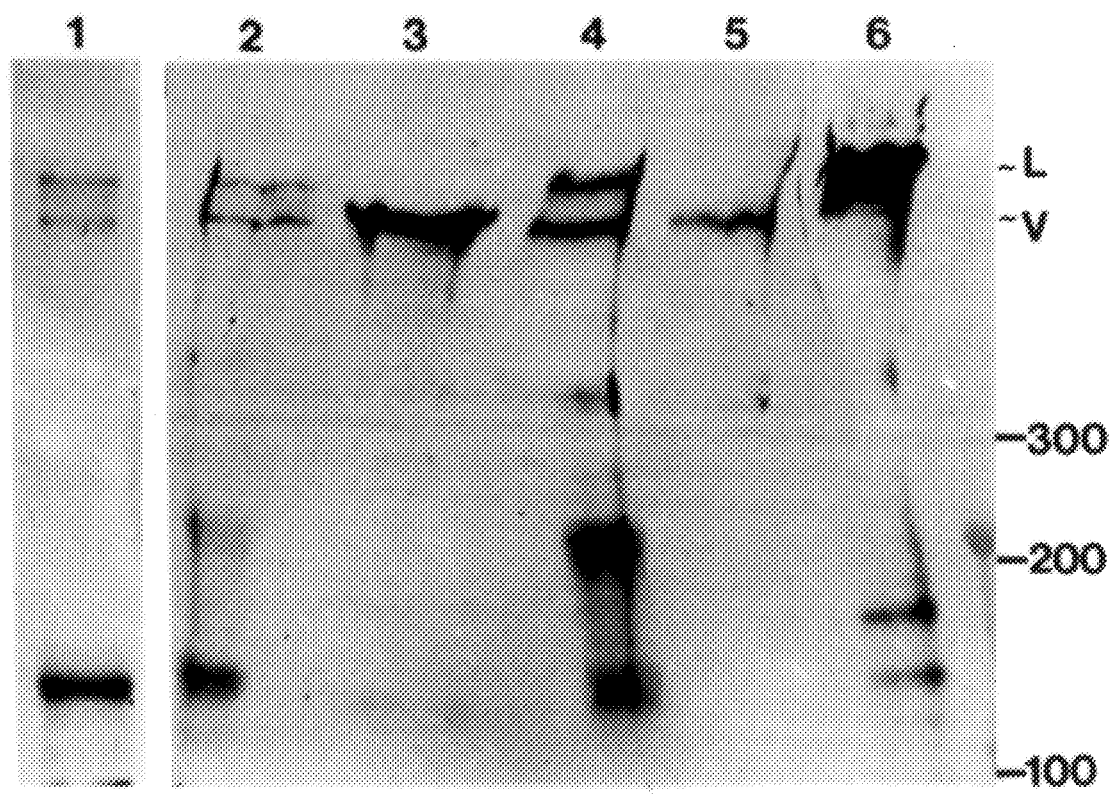
FIGS. 13(A) and (B) show an SDS-PAGE demonstrating laminin, biosynthesis in skin culture.
Figure 13B:
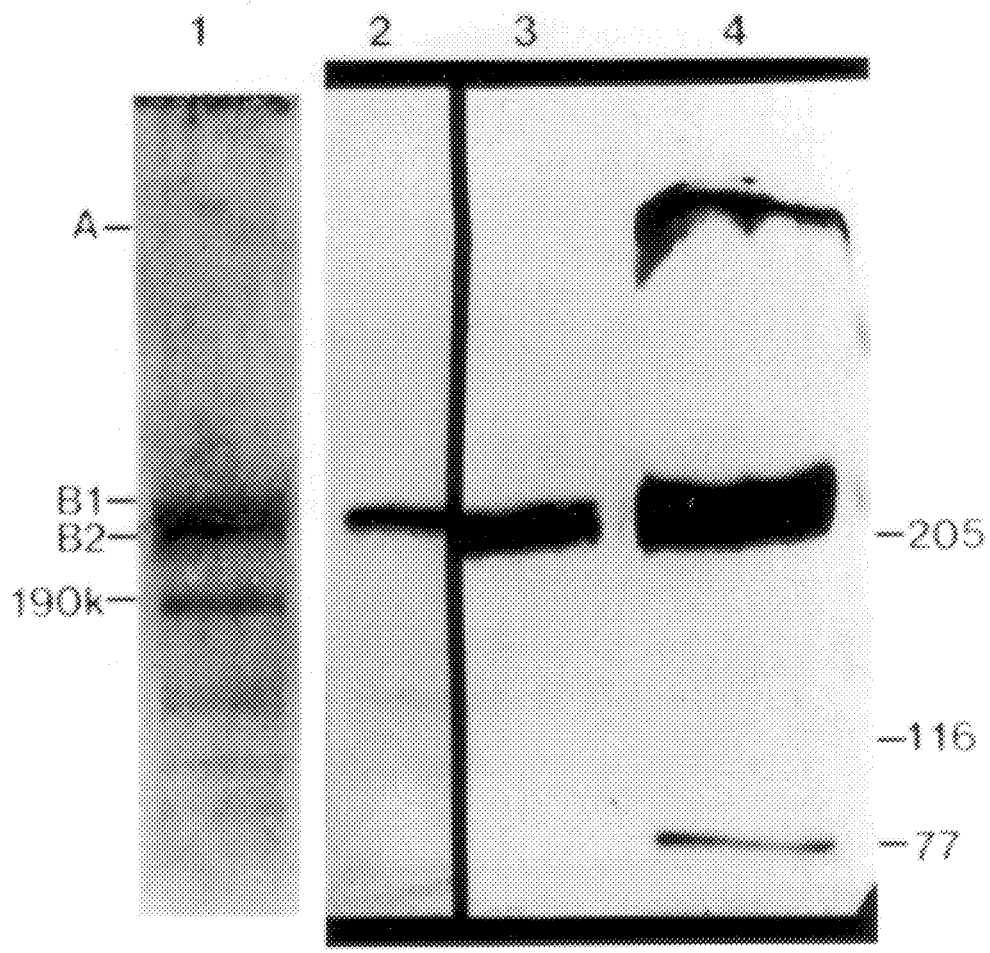

An immunochemical comparison of laminin and k-laminin was performed, and the results are shown in FIG. 13. A nonreduced analysis is shown in FIG. 13A, and a reduced analysis in FIG. 13B. For the nonreduced analysis, human amniotic fluid and squamous cell carcinoma (SCC) conditioned medium were used for affinity chromatography with either 2E8-sepharose (monoclonal anti-laminin B2 chain), or BM165-sepharose (monoclonal anti-kalinin). Lanes 1 and 4 are for the wE8 purified SCC conditioned medium; lane 2 of 2E8 purified human amniotic fluid; lane 3, BM165 antigen purified from human amniotic fluid; lane 5, BM165 antigen purified from SCC conditioned medium; lane 6, laminin from EHS tumor. Samples were separated by nonreduced SDS-PAGE on a 3–5% acrylamide gradient gel and visualized by either Coomassie Blue staining (lane 1) or western blotting with polyclonal anti-laminin antibody (lanes 2,3,4,5 and 6).

Reduced analysis of laminin and the variant is shown in FIG. 13B. The nonreduced variant band derived from SCC conditioned medium shown in FIG. 13A (lane 1, V) was excised from the gel, separated by second dimension SDS-PAGE under reducing conditions and visualized by Coomassie Blue staining (lane 1). Peak fractions from BM165-sepharose purification of SCC conditioned medium (lanes 2/3) and EHS laminin (lane 4) were separated by SDS-PAGE on a 5% acrylamide gel under reducing conditions and transferred to nitrocellulose. The lane containing the SCC derived material (lane 2/3) was cut in half and one half was incubated with mAb545 (lane 2). The other half (lane 3) and lane 4 were incubated with polyclonal anti-laminin antibody.

Conditioned medium from human squamous cell, carcinoma cultures, and human amniotic fluid both were found to be useful for immunoaffinity purification of biochemical quantities of laminin and variant. When conditioned squamous carcinoma cell medium is purified using 2E8-sepharose and the peak elution fraction is separated by non-reduced SDS-PAGE, two high molecular weight laminin species, as well as a 150 kDa band are stained by Coomassie Blue (FIG. 13A, lane 1). Because the 150 kDa band failed to yield lower molecular weight bands on second dimension reduced SDS-PAGE (not shown), we interpret this band to represent nidogen. When the band representing the faster migrating variant species is excised, separated by second dimension reduced SDS-PAGE, and stained by Coomassie Blue, a broad 220–210 kDa band as well as a distinct 190 kDa band are visualized (FIG. 13B, lane 1) analogous to the results obtained with radiolabeled materials in FIG. 11. Thus Coomassie Blue staining reveals that stoichiometrically, the B1, B2 and 190 kDa chains of the faster migrating variant species are present in equal amounts.

Nonreduced western blot analysis (FIG. 13A) of the peak fractions from conditioned squamous carcinoma cell medium and amniotic fluid purified with 2E8-sepharose (lanes 1,3 and 5) and BM165-sepharose (lanes 2 and 4) was done with polyclonal laminin antiserum used as primary antibody. Amniotic fluid (lanes 2 and 3) and squamous carcinoma cell medium (lanes 1,4 and 5) produce essentially identical results in that purification over an anti-laminin B2 chain column produced two nonreduced species and purification over an antikalinin column produced only a single nonreduced species. The higher molecular weight nonreduced species (lanes 1,2 and 4) comigrates with laminin purified from EHS tumor (lanes 6). Analogous to the results with radioactive keratinocyte medium in FIG. 10, the lower molecular weight nonreduced laminin variant species is the only form affinity-purified by BM165-sepharose.

The variant plus kalinin were purified from squamous carcinoma cell culture medium by BM165 affinity chromatography. The disulfide-bond reduced kalinin and variant chains were separated by SDS-PAGE using a wide comb, and transferred to nitrocellulose. The nitrocellulose was then cut through the center of the electrophoretic lane, and one half (FIG. 13B, lane 2) was western blotted using monoclonal antibody 545, specific for the laminin B1 chain. The other half of the lane (lane 3) and a second lane containing EHS laminin chains (lane 4) were blotted with polyclonal anti-laminin. The anti-B1 antibody blots only the upper half of the wide band containing the B chains, while both the B1 and B2 chains are recognized by the polyclonal serum. This result, together with the observation that the variant is immunoprecipitated by anti-B2 monoclonal antibody (FIG. 10, lane 2) indicates that the variant contains authentic B1 and B2 chains. No reaction was noted in the position of the 190 kDa chain, further verifying the immunological distinction of this chain from other EHS laminin subunits.

Anti-B2 chain affinity purified variant and laminin from squamous cell carcinoma conditioned medium as shown in FIG. 13A, lane 1, were visualized by rotary shadow imaging. Pooled peak elution fractions analyzed by Coomassie staining and western blot in FIG. 13A (lanes 1 and 4) were imaged. Cross-shaped molecules closely resembling laminin were readily identified (FIG. 14A). In addition, molecules shown in FIG. 14B were frequently seen. These appear as "Y" shaped molecules similar in size and conformation to the usual cross shaped laminin molecule in that each has one long arm 50 with a large globular domain 52 at its distal end, and two short arms 54, 56 each with two globular domains at their distal ends. The "Y" shaped molecule which we interpret as representing the variant differs from the cross shape of laminin in that there is no third short arm, although some images show that there is a small globular domain 58 present at the intersection of the two short arms 54,56 and the long arm 50.

The difference in molecular weight between the 400 kDa A chain and the 190 kDa variant chain would therefore need to be contained in the third short arm of the laminin cross. The 190 kDa substitution for the A chain contributes the large globule at the distal end of the long arm similar to the structure contributed to laminin by the A chain. The fact that this globule is apparently intact in the variant and antibody 4C7 specifically recognizes this globule on laminin (Engvall et al., J. Cell Biol. 103:2457–2465 (1986)) is further evidence that this chain is a true substitution for the A chain, and not a degradation product.

Figure 15A:
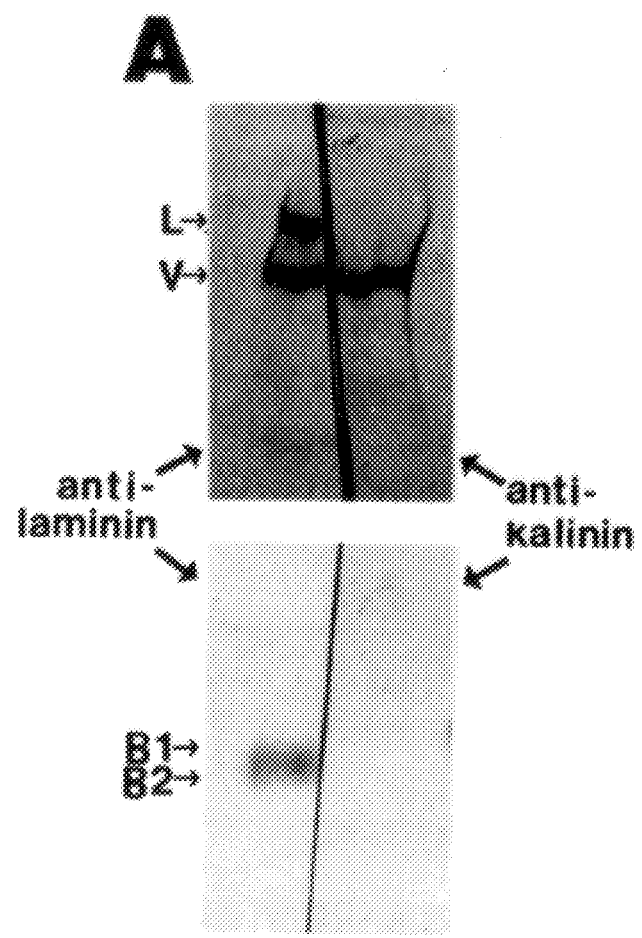
FIG. 15A an SDS-PAGE gel showing comparative immunoblotting of laminin and k-laminin.

An immunological and structural analysis of the laminin variant (k-laminin) and laminin was performed. FIG. 15A was produced by comparative immunoblotting of laminin and the variant. Laminin and variant derived from 2E8-Sepharose (anti-laminin B2 chain) purification of SCC conditioned medium were separated on 3–5% acrylamide gels under nonreducing (upper half) or under reducing conditions (lower half) and electrophoretically transferred to nitrocellulose. The nitrocellulose containing the lanes of both the nonreduced and reduced samples were cut in half. Western blot analysis was then completed with both polyclonal laminin antisera (left halves) and polyclonal kalinin antisera (right halves).

A polyclonal antibody was raised in rabbits to the 400 kDa nonreduced kalinin gel band (Rousselle et al., J. Cell Biol. 114:567–576 (1991)). This antibody identified all kalinin chains by western blotting after disulfide-bond reduction. Laminin and variant were purified from squamous carcinoma cell medium using 2E8-sepharose (anti-B2 chain)

affinity chromatography, and the product was evaluated by SDS-PAGE and western blotting before and after disulfide bond reduction. The nitrocellulose was cut down the center of the two lanes, and one half of each lane was incubated with polyclonal antilaminin, and the other was incubated with the polyclonal anti-kalinin (FIG. 15A). The antilaminin serum identified both laminin and the variant prior to reduction, while the anti-kalinin serum recognizes only the variant.

The lack of reactivity of the anti-kalinin serum with laminin indicates that the crossreactivity with the variant must be with the 190 kDa chain. This crossreactivity is lost upon disulfide bond reduction, and the polyclonal antikalinin serum fails to react with the 190 kDa chain. The immunological crossreactivity suggests that the chains share conformational epitopes but not sequence specific epitopes. The reactivity of the variant with the polyclonal anti-kalinin serum indicates that the 190 kDa variant chain contains epitopes present in the 200 kDa kalinin chain, but absent from the laminin A chain, supporting the conclusion that the variant chain is not a degradation product of the A chain.

Figure 15B:
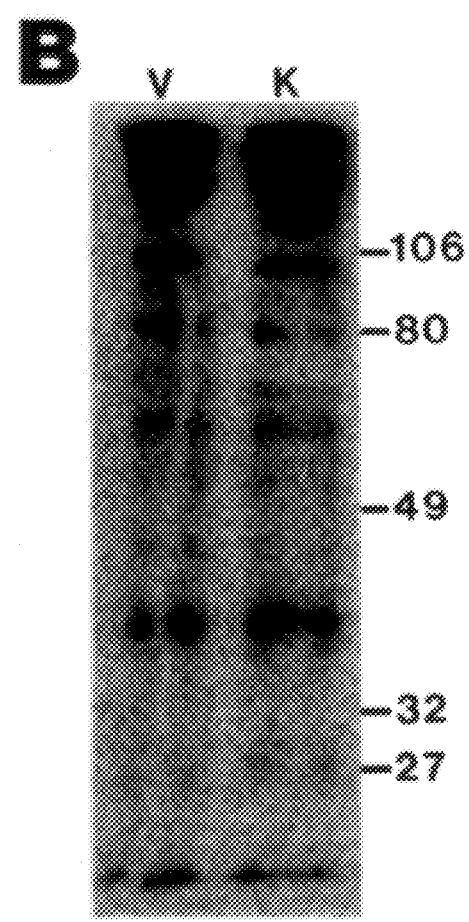
FIG. 15B is an SDS-PAGE gel showing peptide mapping studies using V8 proteases.

Comparison of the peptides generated from V8 protease digestion (FIG. 15B) of the 190 kDa variant chain (V), and the 200 kDa kalinin chain (K), each excised from polyacrylamide gels, indicates nearly identical electrophoretic mobilities. These gels were produced by excising from gels the bands containing the 190 kDa subunit of the variant (lane V) derived from polyclonal anti-laminin immunoprecipitation of radiolabeled keratinocyte medium, and the 200 kDa subunit of kalinin (lane K). The bands were partially digested with V8 protease (2 µg/ml for thirty minutes, at room temperature) and the digestion products separated by SDS-PAGE side by side on a 10% acrylamide gel. These data indicate that these chains are very similar but not identical.

Since the polyclonal anti-kalinin antiserum crossreacts with the variant, the distribution of this reactivity was examined in skin and in brachial plexus nerve (FIG. 16). Frozen 8 µm thick sections of either brachial plexus nerve from a 20 week human fetus (A,C and E) or human neonatal foreskin (B, D and F) were analyzed by indirect immunofluorescent microscopy. A and B were analyzed with polyclonal anti-laminin; C and D with polyclonal anti-kalinin; E with Mab 5H2 anti-merosin; and F with polyclonal anti-kalinin, preimmune serum. The scale bar is 160 µm.

Similar to results seen for kalinin with mAb BM165, the reactivity was restricted to the basement membrane zone of the dermal-epidermal junction of skin (FIG. 16D), and no reactivity was seen above preimmune serum control in brachial plexus nerve (FIG. 16C, 16F). The reactivity of the polyclonal anti-laminin serum reacts with all basement membranes in nerve and skin (FIG. 16A, 16B). The nerve was also intensely stained with B2 chain specific antibodies (not shown) and with anti-merosin (FIG. 16E). This result indicates that the variant is not distributed beyond the dermal-epidermal junction in skin and is not present in peripheral nerve.

The distribution of kalinin, laminin, and variant was similarly analyzed in several other human tissues, and the results are shown in Table 2.

TABLE 2

Tissue Survey°

| Tissue | Antibodies | | |
|---|---|---|---|
| | mAb K140 | polyclonal kalinin | polyclonal laminin |
| skin | +* | +* | + |
| trachea | +* | +* | + |
| large intestine | +* | +* | + |
| small intestine | +* | +* | + |
| lung | +* | +* | + |
| amnion | +* | +* | + |
| peripheral nerve | − | − | + |
| blood vessels | − | − | + |
| skeletal muscle | − | − | + |

*indicates that staining was present only at epithelial-mesenchymal interfaces
°For this survey indirect immunofluorescent microscopy was performed on frozen sections of tissue obtained from a 20 week (estimated gestational age) normal human fetus, except the human amnion which was obtained following a term delivery.

Laminin which is specifically recognized by polyclonal laminin antiserum is clearly reactive in the basement membranes of skeletal muscle, blood vessel endothelium, and as seen in FIG. 16, peripheral nerve. Neither kalinin nor variant are present in these distributions evidenced by lack of immunoreactivity with mAb K140 or with polyclonal kalinin antiserum which recognizes both kalinin and variant. In trachea, large and small intestine, amnion, lung, and skin, polyclonal laminin antiserum reacted with all basement membrane containing structures, while mAb K140 and polyclonal kalinin antiserum reacted only at areas of epithelial-mesenchymal interface. These results indicate that, in the tissues examined, the variant represents a distinct subset of the total laminin distribution, and that the distribution of the variant does not appear to extend beyond that of kalinin.

In summary, k-laminin is a variant of laminin that is restricted in its distribution to the basement membrane zone of the dermal-epidermal junction in skin, and is absent in nonepithelial basement membranes including those of peripheral nerve, skeletal muscle, and blood vessels. The molecule is synthesized by human and bovine keratinocytes, and by a squamous cell carcinoma line. The molecule is also present in amniotic fluid, as is the epithelial specific molecule kalinin (not shown). This variant has a 190 kDa chain substituted for the A chain, which is shorter than the A chain by about 240 kDa, and is immunologically unrelated to the laminin A chain. Instead, the variant 190 kDa chain shows a structural and immunological similarity to the 200/165 kDa chain of kalinin. Visualization of the variant by rotary shadow imaging indicates that the short arm normally contributed by the A chain to laminin is missing in this molecule. However, the substituted 190 kDa chain contributes a large globule at the end of the long arm that appears very much like the domain contributed to normal laminin by the A chain. The presence of this large globule rules out the possibility that the rotary shadowed images represent B1–B2 chain dimers, consistent with the observation that none of these dimers were detected in the cell media preparations.

A "Y" shaped laminin variant has been previously reported as a product of rat schwannoma cells. This schwannoma molecule lacks the laminin A chain and instead contains additional peptides of 130 and 35 kDa (Davis et al., J. Neurosci. 5:2662–2671 (1985)). The schwannoma laminin variant thus differs structurally from k-laminin, and in the biological distribution of the molecules. K-laminin is not found in peripheral nerve tissue. Polyclonal anti-kalinin crossreacts with skin cell derived variant, but is unreactive with peripheral neural tissue. This failure of polyclonal anti-kalinin to crossreact with peripheral nerve tissue shows that k-laminin and the schwannoma variant are immunologically distinct. The skin variant is not related to the schwannoma produced variant.

Rat astrocytes also synthesize a laminin variant lacking the A chain but no substituted chain was observed in the astrocyte variant (Liesi and Risteli, *Exp. Neurol.* 105:86–92 (1989)). 3T3-L1 adipocytes produce a molecule with a 200 kDa chain substituted for the A chain (Aratani and Kitigawa, *J. Biol. Chem.* 263:16163–16169 (1988), but k-laminin is not believed to be present in adipocytes. Other laminin variants with substituted A chains include merosin (Ehrig et al., *Proc. Natl. Acad. Sci.* 87:3264–3261 (1990)) and mouse heart laminin (Paulsson and Saladin, *J. Biol. Chem.* 264:18726–18732 (1989)), but both of these molecules retain the three short arms reminiscent of EHS laminin.

Previous evaluation of laminin synthesized by both malignant and nonmalignant keratinocytes showed association of laminin with additional glycoproteins (Frenette et al., *Cancer Research* 48:5193–5202 (1988)). The data support the coprecipitation of laminin, the keratinocyte variant, and kalinin by the anti-laminin serum. As described below, laminin becomes covalently associated with the kalinin glycoprotein.

Woodley et al., *J. Cell. Physiol.* 136:140–146 (1988) have reported that EHS laminin inhibits keratinocyte migration. The inhibitory activity of this laminin is believed to reside in a fragment of the A chain. Absence of the A chain in the variant is believed to facilitate cell migration, as compared to laminin. Hence the k-laminin adhesion molecule can be exogenously supplied between transplanted keratinocytes and an underlying dermis to improve adhesion of the keratinocytes without inhibiting keratinocyte cell migration.

Covalent Association Between Kalinin and K-laminin

When kalinin is isolated directly from human amnion, kalinin chains and laminin variant chains are consistently found complexed into a disulfide bonded aggregate that enters only dilute polyacrylamide gels. This isolated covalent complex of kalinin and k-laminin is a novel molecule.

To demonstrate this covalent association, human amniotic membranes were extracted with bacterial collagenase as previously described in Bächinger et al., *J. Biol. Chem.* 256:10095–10101 (1990), as modified in applicants' incorporated U.S. patent application Ser. No. 07/936,850 now U.S. Pat. No. 5,352,668. First, the proteins were precipitated from the initial soluble fraction by the addition of ammonium sulfate to a final concentration of 30% (w/v) and incubated overnight at 4° C. Precipitated materials were recovered following centrifugation (17,000×g for 60 minutes) and resuspended in chromatography buffer prior to dialysis. Insoluble material was removed from the sample by ultracentrifugation, for one hour at 18,000 rpm in a type 19 rotor (Beckman Instruments), just prior to affinity chromatography on a type VIII specific mAb column. The unbound fraction from this step was then applied to a K140-sepharose column, washed, eluted, and peak fractions obtained. Peak fractions were treated with diisopropyl fluorophosphate (5 µg/ml), dialyzed against water, and stored at −70° C. until use. Kalinin was therefore purified from the soluble fraction by affinity chromatography using monoclonal antibodies directed against kalinin.

Figure 17:
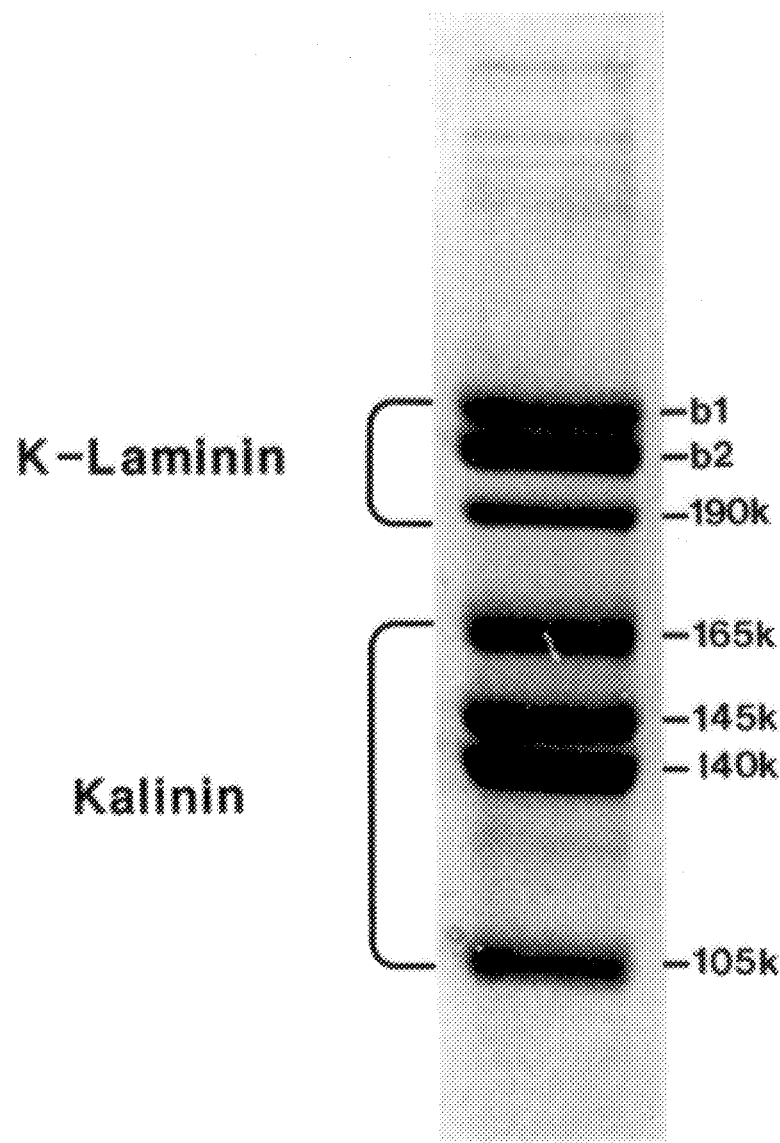
FIG. 17 is an electrophoretic analysis of k-laminin and kalinin that has been affinity purified from amnion extracts using monoclonal antibodies against kalinin.

Electrophoretic analysis of this purified material is shown in FIG. 17. Subunits of both kalinin (bands at 165K, 145K, 140K and 105K) and k-laminin (B1, B2 and 190K) were identified. Initially mAb BM165, which recognizes the 165K subunit of kalinin and has been shown to crossreact with the 190K subunit of k-laminin, was used in this purification. This crossreactivity of BM165 would explain the presence of both kalinin and k-laminin in these preparations. However, the same results were obtained with mAb K140, which recognizes the 140K subunit of kalinin and does not crossreact with k-laminin. The stable association of kalinin and k-laminin accounts for the presence of both kalinin and k-laminin subunits in the preparation even though the mAb only reacts with kalinin.

Figure 18:
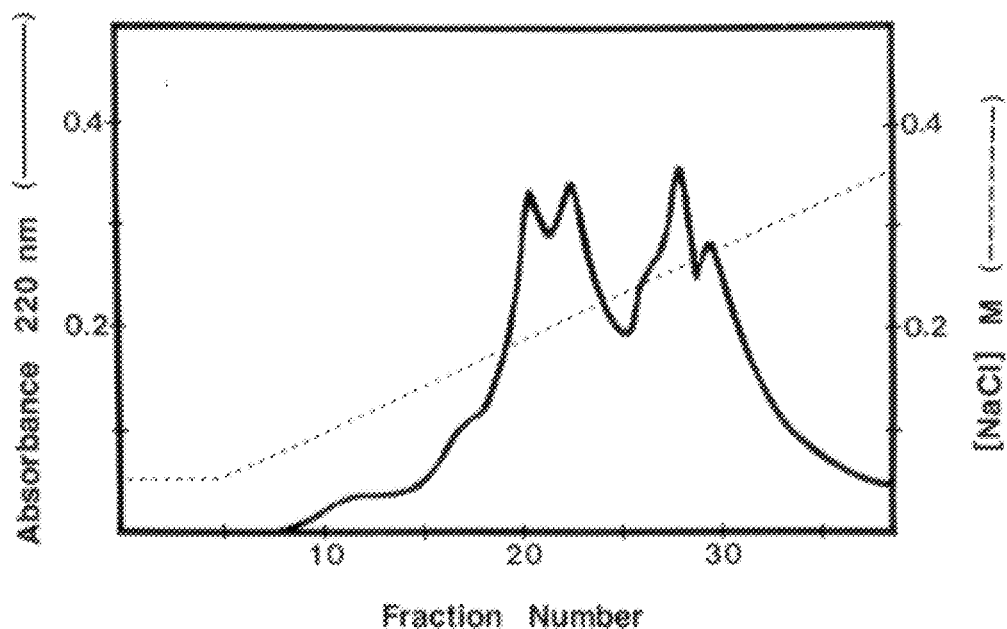
FIG. 18 (A) is a graph showing fractionation of kalinin and k-laminin/kalinin adduct, while FIG. 18 (B) is a non-reduced electrophoretic analysis of the material.
Figure 18:
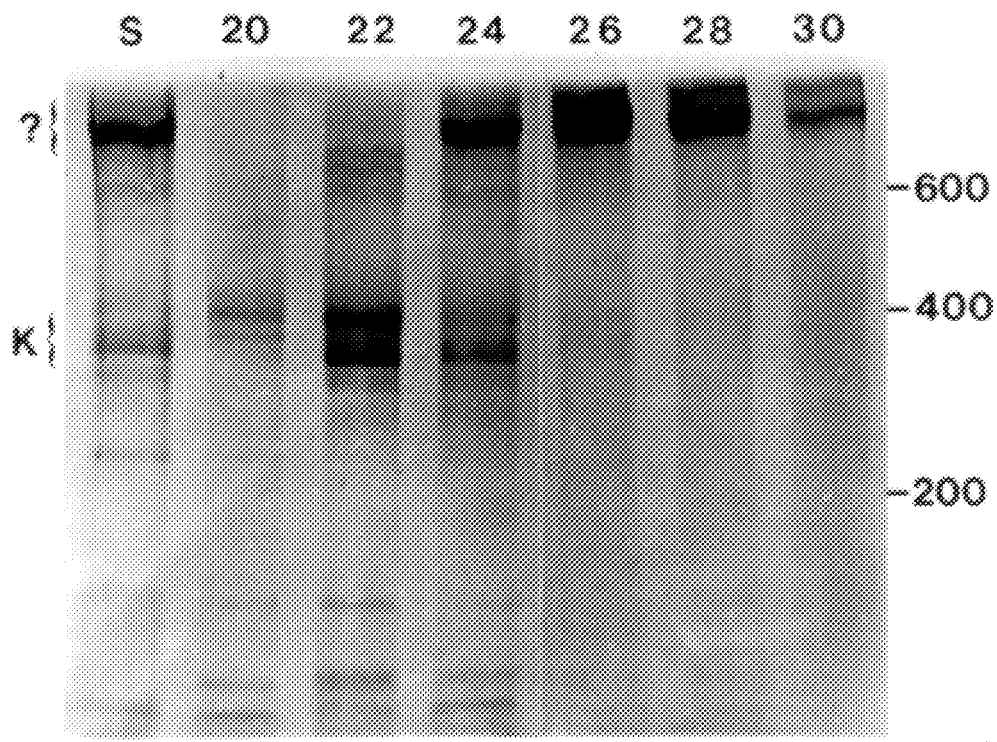

Further analysis of this affinity purified material by ion exchange chromatography is shown in FIG. 18A. This material could be fractioned into essentially two peaks. Electrophoretic analysis of separated materials under non-reducing conditions indicates that the first peak contains material equivalent to kalinin present in keratinocyte culture media. Material in the second peak represented a very high molecular weight complex which barely entered the gel. Electrophoretic analysis of material in peak 2 after reduction gave the same pattern of seven bands seen in FIG. 17.

Figure 19:
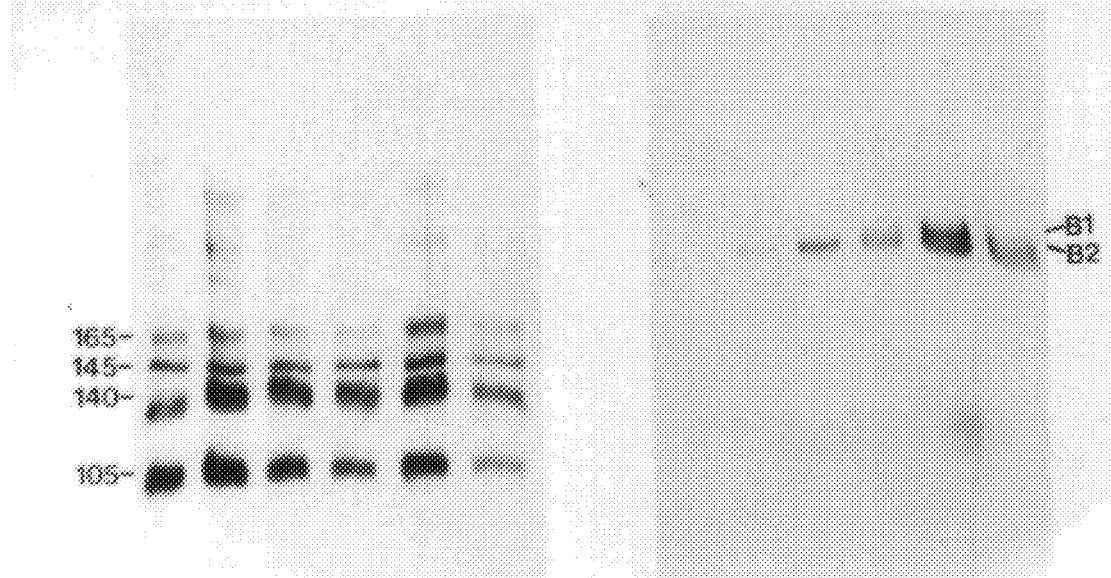
FIG. 19A, FIG. 19B, FIG. 19C, and FIG. 19D show western blot analyses of immunoaffinity purified k-laminin/kalinin adduct using polyclonal antibodies against kalinin and laminin.

Immunochemical analysis of these materials using polyclonal antibodies against kalinin and laminin is presented in FIG. 19. Samples from the indicated fractions were separated by reduced and non-reduced electrophoresis and western blot analysis was performed with polyclonal anti-kalinin and polyclonal anti-laminin. The material in peak 1 was identified as kalinin only and laminin B chains were not found (FIGS. 19A and 19C). The high molecular weight material from peak 2 was identified by both kalinin and laminin antibodies (FIG. 19B). After reduction with 2-mercaptoethanol, both kalinin and laminin B1 and B2 chains were identified in peak 2 material (FIG. 19C and 19D). These results are consistent with the identification of a high molecular weight complex containing both kalinin and k-laminin.

Figure 20:
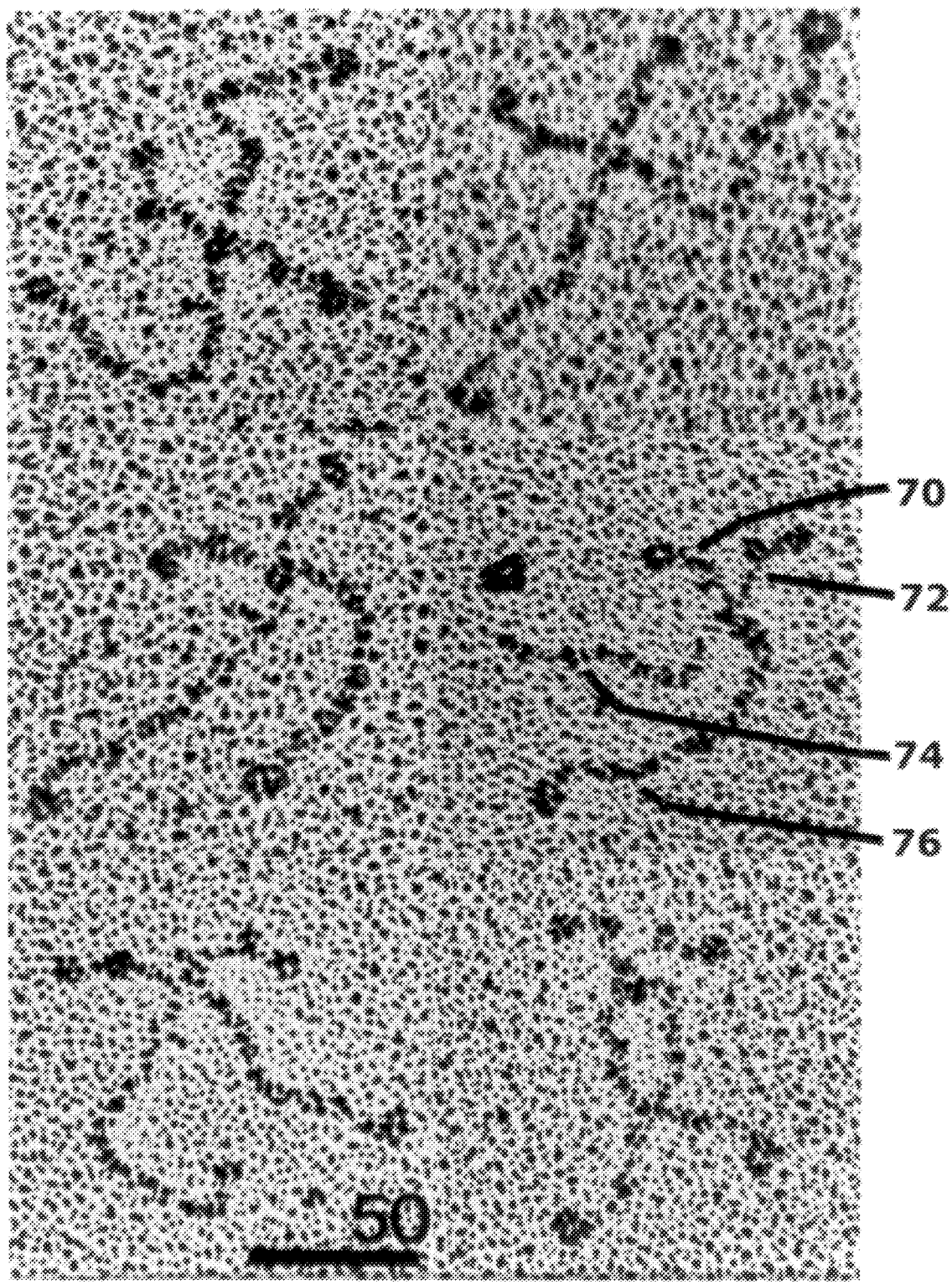
FIG. 20 is a rotary shadow image analysis of the complex present in peak 2 of FIG. 18 (A).
Figure 21:
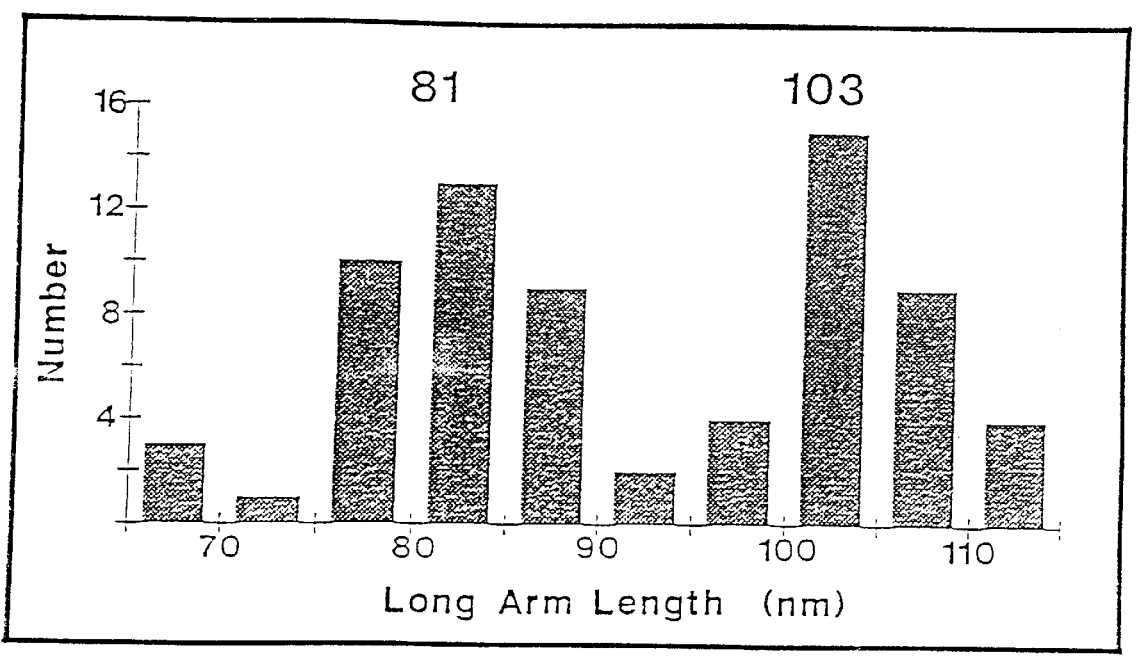
FIG. 21 is a graph showing the distribution of long arm lengths in the rotary shadow image analysis of FIG. 20.

Further confirmation of the kalinin and k-laminin complex was obtained by rotary shadow image analysis. Images of material from peak 2 (fraction 28) of FIG. 18A are presented in FIG. 20. Representative assemblies are characterized by having two short arms 70, 72 and two long arms 74, 76. The lengths of the long arms 74, 76 give a bimodal distribution shown in FIG. 21. The 81 nm length of the first long arm is consistent with the previously determined length of the long arm of k-laminin, while the 103 length of the other long arm is consistent with the length of a kalinin molecule. Taken together, this and the results presented above indicate that kalinin and k-laminin are assembled and covalently associated in tissue.

Cultured Epidermal Keratinocyte Transplantation

Methods of transplanting keratinocytes have already been disclosed in the literature, and any of these methods are suitable for modification according to the present invention. Knowledge of how such transplants are generally performed is within the purview of persons skilled in the art. However, by way of illustration, several examples of suitable transplant methods are disclosed.

EXAMPLE 1

One method of keratinocyte transplantation was disclosed by O'Connor et al., *The Lancet* 1:75–78 (19381). A patient had two 2 cm² skin samples removed under local anesthesia.

The tissue was placed in culture medium and transferred to a laboratory for cultivation and graft preparation. As much subcutaneous tissue and dermis as possible was removed from the tissue, and the tissue was then minced and trypsinized. The cells were inoculated at different densities (from $10^4$ to $10^6$ per 50-mm diameter dish containing $4 \times 10^5$ lethally irradiated 3T3 cells). The cultures were supplied with fortified Eagle's medium supplemented with 20% fetal calf serum, 0.4 μg/mL hydrocortisone, and 0.1 nmol/L choleragen. The cultures were incubated at 30° C. in a 10% $CO_2$ atmosphere. After three days, epidermal growth factor (EGF 10 ng/mL) wets added to the culture medium. The medium was changed twice weekly until the cultures either became confluent (between 14 and 21 days) or were subcultured. Some subconfluent cultures were viably frozen and later subcultured. In this way, secondary and tertiary subcultures could be prepared for later use as grafts.

The confluent epithelial cells were detached in their confluent state from the surface of the culture dishes using the enzyme dispase. After detachment, each elastic epithelium shrank to a diameter of 2 to 2.5 cm. Each epithelium was then washed with serum-free medium and placed basal-side up on two layers of sterile vaseline gauze cut into 2-cm diameter circles. Sufficient serum-free medium was added to cover the exposed basal surface. Several dishes containing grafts were then placed in a glass jar; the atmosphere in the jar was flushed with 10% $CO_2$ and the sealed jar was transported to the bedside.

Epithelial grafts including the vaseline gauze covering were placed on prepared wound sites with the basal cell layer directed against the wound surface. No suturing was necessary because the grafts were held in place by a single layer of non-impregnated fine mesh gauze, which was overlayed with a loose layer of coarse mesh gauze that was changed daily. The fine mesh gauze and the vaseline gauze were removed between the sixth and tenth days and the area was redressed with a single layer of vaseline gauze and a loose layer of coarse gauze. These dressings were changed daily for three to four weeks from the time of grafting. Thereafter, the grafts were left exposed to the atmosphere, but treated with a thin layer of lanolin ointment once daily.

The epithelial grafts described above were placed on three different types of "recipient beds" (wound surfaces): early granulation tissue (less than 7 days old), chronic granulation tissue, and areas recently excised down to the facia.

In accordance with the present invention, adhesion of the confluent epithelium to the underlying tissue is improved by spreading a thin layer of exogenous kalinin either on the basal face of the keratinocyte culture or on the epithelium of the exposed surface of the tissue on which the graft was being placed. Such exogenous kalinin would provide superior adhesion because (a) the confluent keratinocytes in cell culture have stopped or significantly decreased kalinin production; (b) kalinin originally present on the basal surfaces of the cultured cells was destroyed by the dispase treatment; and (c) kalinin is necessary for stabilization of the dermal-epidermal junction.

Alternatively, exogenous kalinin or the covalently complexed kalinin/k-laminin is applied between the cultured keratinocytes and the epithelium. The kalinin, or k-laminin, or covalent complex is preferably applied in a pharmaceutically acceptable carrier, such as PBS containing physiological amounts of $Ca^{++}$ and $Mg^{++}$ (e.g., 0.7–1.1 mmol/L $Mg^{++}$ and 1–3 mmol/L $Ca^{++}$). The adhesion proteins can be suspended in PBS with $Ca^{++}$ and $Mg^{++}$, then introduced into a gelatin or propylene glycol base for topical application.

EXAMPLE 2

Methods of grafting autologous cultured human epithelium were also disclosed in Gallico et al., *New Eng. J. Med.* 311:448–451 (1984). The patients were two children who sustained burns on more than 95% of their bodies, but had half or more of their body surfaces successfully covered with cultured epithelial autografts. On admission, a 2 $cm^2$ full-thickness biopsy specimen of skin was removed from the axilla of each patient. The skin was minced and trypsinized to produce a single cell suspension. Aliquots of $2 \times 10^6$ cells were frozen and stored or cultured in flasks with a surface area of 75 $cm^2$. When the colonies became confluent at 10 days, the cultures were trypsinized, and $3 \times 10^5$ cells were inoculated to make secondary and tertiary cultures for grafting. To prepare grafts, the cultured sheets of cells were released from the flasks with dispase, washed with medium, and applied to petrolatum gauze cut to 4.5×6 cm. The burn wounds had been excised to muscle fascia, except for third-degree facial burns, which were excised tangentially to a depth sufficient to remove dead tissue. The cultured grafts with their gauze backing were placed on prepared wound surfaces, sutured in place, and dressed with dry gauze. The petrolatum gauze was removed seven to ten days later.

According to the present invention, the foregoing procedure would be modified by amplifying the expression of kalinin by treatment of the released keratinocytes with a cytokine yet to be identified. Since kalinin production appears to be linked to cell proliferation, growth hormones may be possible candidates. Altered feeding schedules might also be effective.

EXAMPLE 3

Transplants of autologous cultured human epithelium can be performed as in Examples 1 and 2, above. According to the present invention, the methods are modified by transplanting the keratinocytes while a substantial number of the cells are still actively producing kalinin. In this case, subconfluent keratinocytes are released from the culture substrate by treatment with 10-mM EDTA. The suspended cells are washed with growth medium and suspended in Vitrogen (Collagen Corporation, Palo Alto, Calif.) and poured onto a layer of gauze in teflon forms to produce a thin stabilized layer of single keratinocytes. The Vitrogen is gelled by brief incubation at 37° C., and the gel is lifted from the forms and applied to the wound bed. The transferred cells are protected as in Examples 1 and 2.

In view of the observation that kalinin is synthesized only by dividing keratinocytes, it is important to consider the state of confluence of cells to be used for successful re-epithelialization of burn wounds. Thus, kalinin may be deficient or altered in individuals with certain blistering conditions such as junctional epidermolysis bullosa (Eady, *Clin. Exp. Dermatol.* 12:161–170 (1987)) or herpes gestationis (Katz et al. (eds.), *Dermatology in General Medicine*, McGraw-Hill, N.Y., 586–588 (1987)). Hence, topical application of kalinin (or substances such as k-laminin that contain kalinin) may also be useful in treating these conditions to improve adherence between the dermis and epidermis.

EXAMPLE 4

Standard in vitro attachment assays have been performed to determine that purified kalinin facilitates keratinocyte attachment to plastic substrates. In these assays, exogenous purified kalinin or control proteins are incubated overnight with the substrate, and the plates are then washed. Unattached cells are washed away, and the remaining attached cells are quantified, as described in Aumailley et al., *Exp. Cell. Res.* 181:463–474 (1989).

EXAMPLE 5

The role of kalinin or k-laminin in enhancing keratinocyte attachment to a substrate is also demonstrated by treating cell sheets with dispase to release them from a plastic or glass substrate, as would be done in preparing transfer sheets to a wound bed The sheet is then transferred to a series of plastic substrates which are coated either with kalinin or controlled proteins. The adherence of the cell sheet is evaluated morphologically to demonstrate that the sheet has superior adherence to the kalinin-coated substrate. The adherence of the sheet is also evaluated by indirect immunofluorescence using the BM165 mAb. Firmly attached cell sheets will not allow antibody penetration to the substrate surface as demonstrated by the studies of confluent keratinocyte cultures. Fluorescence beneath the cells would be observed for less firmly attached sheets.

EXAMPLE 6

This example demonstrates the phase of the cell cycle during which kalinin is synthesized by cultured keratinocytes. Single keratinocytes are plated at various times after culturing begins, and kalinin is localized immunochemically within cells or upon the substrate. Intracellular kalinin is present only within single cells or small clusters of keratinocytes. It is not found intracellularly within the keratinocytes that are in the central regions of large colonies, but only at the periphery where cells are still dividing and migrating.

At various times, cultures are incubated with radioisotopic protein precursors for twelve hours at selected times after plating. Kalinin is then quantitatively immunoprecipitated as a function of total time in culture. The preliminary results of the experiments show that kalinin synthesis decreases with time in culture when measured on a per cell basis. This information will define the optimal time of cell culture to maximize kalinin production and deposition by keratinocytes.

The present invention includes kalinin from both human and animal sources. Kalinin is present in (and can be purified from) such diverse sources as fetal calf, human amnion and amniotic fluid.

In the future, technical advancements may also permit identification, isolation and purification of individual domains of kalinin which provide keratinocyte adhesion. These domains can be identified by fragmentation of isolated kalinin to produce individual domains, and individualized testing of each domain's ability to function as a keratinocyte-attachment factor. Alternatively, domain specific monoclonal antibodies that block cell adhesion could be generated and used to identify the active domain or domains. Once these advances have taken place, the isolated adhesion domains can be purified and used in the present invention.

Future advances may also permit molecular cloning of kalinin, kalinin sub-chains, or related proteins or glycoproteins that provide keratinocyte adhesion. These cloned chains will provide structural information about the identified structural domains. The cloned domains can then be expressed in vitro. If the cell attachment domain is contained within a single kalinin chain, it is possible that a functional fragment could be produced in vitro. Recombinant protein fragments would be transfected into CV-1 cells using the SV40 virus vector as described in Kriegler et al., *Gene Transfer and Expression*, Stockton Press, New York (1990).

Animal Studies

Animal studies can be performed to show the effectiveness of kalinin or the kalinin/k-laminin adduct to promote the adhesion of human keratinocytes to a wound bed. Suitable wound beds include areas of excised epidermis, or burns that have left an underlying dermal area exposed.

EXAMPLE 7

Human keratinocytes derived from neonatal foreskin and from tissue pieces obtained from discarded surgical specimens are expanded in cell culture using standard conditions. Cells are grown to subconfluence and then harvested using EDTA dissociation, or will be grown to superconfluence and the resulting cell sheets will be dissociated using dispase.

Kalinin and k-laminin will be purified from the spent medium of cultured keratinocytes, KB cells, WISH cells or squamous carcinoma cell line 25, whichever produces the largest quantities, using immuno-affinity columns bearing the BM-165 monoclonal antibody that recognizes the "A"-like chain of kalinin and k-laminin. Both molecules will be retained by the matrix and eluted with 0.1M acetic acid and immediately neutralized. The mixture of k-laminin and kalinin will be further fractionated by immuno-affinity with a column bearing the BM-140 monoclonal antibody that recognizes only the "B1"-like chain of kalinin. Pure kalinin will be eluted from the column, while purified k-laminin will be contained in the flow through. The procedure will be repeated until pure k-laminin is obtained as judged by western analysis. The kalinin-k-laminin adduct will be purified using the BM-165 mAb affinity matrix. The adduct will be solubilized from human amnion following extensive collagenase digestion as described by Bächinger (1990) and applicants' U.S. patent application Ser. No. 07/936,850, now U.S. Pat. No. 5,352,668, which have been incorporated by reference. If insufficient amount of kalinin and k-laminin can be obtained from cultured cells, the disulfide bond joining the two molecules in the purified adduct can be selectively reduced by incubation with 1–10 mM cysteine, while retaining the native conformation. The reduction products will be fractionated as described above.

Nude mice each receive 4 full thickness skin wounds 1 $cm^2$ each. The wounds are administered on the back, two on each side of the spinal midline under anesthesia. The wounds are immediately be treated as described below, and the mice are allowed to recover for 1–5 days under mild anesthesia to prevent trauma to the wound surface.

On days 1–5, the mice are sacrificed by anesthesia overdose and the wound surfaces will be evaluated for uniform adhesion of the applied human keratinocytes by standard histology, supplemented by immunohistochemistry to ensure the human origin of the attached cells. The probes are human-specific anti-keratin antibodies.

The sections will be scored by the percentage of epidermal attachment versus detachment along the wound surface.

Kalinin, k-laminin and the kalinin-k-laminin adduct will be individually evaluated. The molecules will be dissolved in PBS containing physiological amounts of $Ca^{++}$ and $mg^{++}$, at concentrations of 0, 1, 2.5, 5 and 10 µg/ml. (Examples of physiologic amounts are 0.7–1.1 mmol/L $Mg^{++}$ and 1–3 mmol/L $Ca^{++}$).

1. Keratinocyte sheets

The 0 µg/ml solution will always be applied to wounds on the left side of the mouse. Test solutions of each molecule will be applied to the right side wounds. Immediately following wounding, keratinocyte sheets will be applied to the surface of the wounds on both sides of the mouse, and the wounds will be covered with Vaseline coated gauze. One mouse per molecular concentration will be used.

2. Keratinocyte suspensions

Dispersed keratinocytes will be suspended in 0.2% gelatin, PBS plus $Ca^{++}$ and $Mg^{++}$ at 37° C. To separate portions of the suspension, each of the test molecules will be added to the final concentrations of 0, 1, 2.5, 5, and 10 µg/ml. The suspension will be immediately poured into forms containing a hydrophobic surface, layered with nylon mesh. The plates will be cooled to 4° C. to allow the gelatin to solidify. The gel will then be covered with Vaseline-coated gauze and applied to the wound surface.

The gel-suspensions will be applied to the fresh wounds. The 0 µg/ml molecular suspension will always be applied to wounds on the left side of the mouse. One mouse per molecular concentration will be used.

Definitions

As used in this specification, an antigen is "immunoreactive" with a monoclonal antibody if it is immunoprecipitated by the monoclonal antibody, for example in SDS-PAGE.

An "isolated" protein, such as isolated k-laminin, is substantially one that is sufficiently purified that it is substantially free of other proteins that it is associated with in vivo. An example of an isolated molecule is one that has been subjected to immunoaffinity separation to separate substantially all proteins except for the isolated species. The covalently associated kalinin-k-laminin is isolated when it is substantially free of other proteins that are found in the environment of this complex in vivo.

Electrophoresis bands are substantially electrophoretically identical when they produce substantially identical band patterns when exposed to and reacted with identical monoclonal antibodies.

Reaction between a monoclonal antibody and an antigen refers to an antigen-antibody interaction.

Reduction under conditions that break disulfide linkages includes exposure to 2-mercaptoethanol.

An adduct is a covalently bound complex.

Having illustrated and described the principles of the invention in several preferred embodiments, it should be apparent to those skilled in the art that the invention can be modified in arrangement and detail without departing from such principles. We claim all modifications coming within the spirit and scope of the following claims.

We claim:

1. A purified protein preparation comprising a heterotrimeric laminin variant linked by a disulfide bond to kalinin, wherein the heterotrimeric laminin variant is of molecular weight about 650 kDa and comprises:

a first subunit substantially identical to a B1 chan of EHS laminin;

a second subunit substantially identical to a B2 chain of EHS laminin; and a third subunit of about 190 kDa that is specifically recognized by monoclonal antibody BM165 (ATCC Accession Number);

and wherein the kalinin molecules has a molecular weight of about 410–460 kDa, and separates into electrophoretic fragments of about 165 kDa, 145 kDa, 140 kDa and 105 kDa under reducing conditions.

2. A method of improving the adhesion of epidermal cells to an underlying dermal substrate comprising providing a purified protein preparation of claim 1 between the epidermal cells and the dermal substrate.

3. A method of improving the adhesion of epidermal cells to an underlying dermal substrate, the method comprising providing between the epidermal cells and the dermal substrate a purified preparation of an isolated heterotrimeric laminin variant of molecular weight about 650 kDa wherein said laminin variant comprises:

a fist subunit substantially identical to a B1 chain of EHS laminin;

a second subunit substantially identical to a B2 chain of EHS laminin; and a third subunit of about 190 kDa that is specifically recognized by monoclonal antibody BM165 (ATCC Accession Number).

* * * * *

UNITED STATES PATENT AND TRADEMARK OFFICE
CERTIFICATE OF CORRECTION

PATENT NO. : 5,770,562
DATED : June 23, 1998
INVENTOR(S) : Burgeson et al.

Page 1 of 2

Figure 1B:
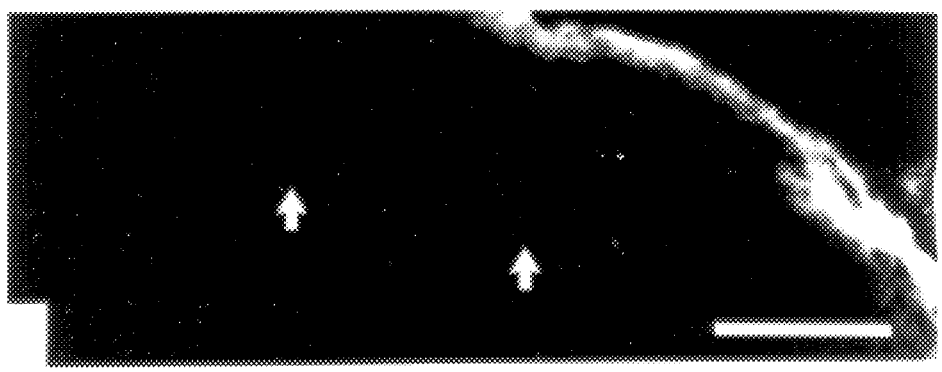
FIG. 1B shows the frozen section stained with media from unfused myelomas.

It is certified that error appears in the above-identified patent and that said Letters Patent is hereby corrected as shown below:

| Col./Line | Error Reads | Should Read |
|---|---|---|
| 7/9 | FIG. 15A an | FIG. 15A is an |
| 7/19 | FIG. 16C and FIG. 16D; | (FIG. 16C and FIG. 16D); |
| 8/25 | 10195 | 10095 |
| 11/21 | FIG. 1B. | FIG. 1B). The BM165 Hybridoma was deposited with the American Type Culture Collection (ATCC), 12301 Parklawn Drive, Rockville, Maryland 20852, on December 31, 1997. The deposit has been accorded ATCC designation HB-12453. |
| 11/22 | Mab | mAb |
| 13/12 | Mab- | mAb- |
| 13/16 | Mab. | mAb. |
| 13/33 | anti-type-VIII | anti-type-VII |
| 13/36 | Mab | mAb |
| 13/67 | distributed. | distributed |
| 15/5 | aware | aware. |
| 16/38 | mabs | mAbs |
| 16/55 | 15865 | 1586 |
| 17/44 | 35, S- | 35 S- |
| 18/4 | 40° C. | 4° C. |
| 19/56 | anti-laminin | anti-laminin. |
| 21/31 | cell, | cell |
| 22/15 | B2 | B2 |
| 25/13 | 1988) | 1988)) |
| 25/16 | 3261 | 3268 |
| 26/44 | 70, 72 | 70, 72 |
| 26/45 | 74, 76 | 74, 76 |
| 26/66 | (19381) | (1981) |
| 27/12 | wets | was |

UNITED STATES PATENT AND TRADEMARK OFFICE
CERTIFICATE OF CORRECTION

PATENT NO. : 5,770,562

DATED : June 23, 1998

Page 2 of 2

INVENTOR(S) :
Burgeson et al.

It is certified that error appears in the above-identified patent and that said Letters Patent is hereby corrected as shown below:

| | | |
|---|---|---|
| 28/65 | in vitro | *in vitro* |
| 29/12 | bed  The | bed.  The |
| 29/66 | in vitro | *in vitro* |
| 30/1 | in vitro | *in vitro* |
| 31/29 | is substantially one | is one |
| 32/22 | Accession Number); | Accession Number HB-12453); |
| 32/44 | Accession Number); | Accession Number HB-12453); |

Signed and Sealed this

Twenty-second Day of May, 2001

Attest:

NICHOLAS P. GODICI

Attesting Officer

Acting Director of the United States Patent and Trademark Office